(12) United States Patent
Donohue et al.

(10) Patent No.: US 10,604,757 B2
(45) Date of Patent: Mar. 31, 2020

(54) BIOLOGICAL CONTROL OF COLEOPTERAN PESTS

(71) Applicants: SYNGENTA PARTICIPATIONS AG, Basel (CH); SYNGENTA CROP PROTECTION LLC, Greensboro, NC (US)

(72) Inventors: Kevin V. Donohue, Durham, NC (US); Renshui Liu, Cary, NC (US); Jeng Shong Chen, Durham, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/537,036

(22) PCT Filed: Nov. 17, 2015

(86) PCT No.: PCT/US2015/060989
§ 371 (c)(1),
(2) Date: Jun. 16, 2017

(87) PCT Pub. No.: WO2016/105696
PCT Pub. Date: Jun. 30, 2016

(65) Prior Publication Data
US 2018/0216105 A1 Aug. 2, 2018

Related U.S. Application Data

(60) Provisional application No. 62/096,491, filed on Dec. 23, 2014.

(51) Int. Cl.
C12N 15/113 (2010.01)
C12N 15/82 (2006.01)
A01N 57/20 (2006.01)

(52) U.S. Cl.
CPC ............ *C12N 15/113* (2013.01); *A01N 57/20* (2013.01); *C12N 15/8218* (2013.01); *C12N 15/8286* (2013.01); *C12N 2310/14* (2013.01); *Y02A 40/162* (2018.01)

(58) Field of Classification Search
CPC .................................................. C12N 15/113
USPC ......................................................... 800/302
See application file for complete search history.

(56) References Cited

U.S. PATENT DOCUMENTS 8,445,666 B2   5/2013   Rigoutsos et al.

FOREIGN PATENT DOCUMENTS

| EP | 2213738 A2 | 8/2010 |
|---|---|---|
| WO | 2005049841 A1 | 6/2005 |
| WO | WO 2005/049841 * | 6/2005 |
| WO | 2013192256 A1 | 12/2013 |
| WO | 2014153254 A2 | 9/2014 |

OTHER PUBLICATIONS

Thomas et al. 2001, The Plant Journal 25(4):417-425.*
Somma et al., PLOS Genetics, vol. 4, No. 7, Jul. 18, 2008, p. e1000126.
Database EMBL [Online], XP002752891, retrieved from EBI accession No. EMBL:JQ581037, Feb. 8, 2012.
Warner et al., Molecular Cell, vol. 28, No. 4, Nov. 29, 2007, pp. 692-699.
Braunschweig et al., EMBO Journal, vol. 28, No. 23, Dec. 2, 2009, pp. 3635-3645.
Rodrigues et al., PLOS One, vol. 9, No. 10, Oct. 30, 2014, p. e109825.
Chu et al., Pesticide Biochemistry and Physiology, vol. 110, Feb. 27, 2014, pp. 1-6.
Katoch et al., Applied Biochemistry and Biotechnology, vol. 141, No. 4, Aug. 1, 2013, pp. 847-873.
Zhang et al., Insect Science, vol. 20, No. 1, Jun. 12, 2012, pp. 15-30.
International Search Report for International Application No. PCT/US2015/060989 dated Jan. 26, 2016.

* cited by examiner

*Primary Examiner* — Li Zheng
(74) *Attorney, Agent, or Firm* — Amy Krom

(57) ABSTRACT

Disclosed are double stranded RNA molecules that are toxic to coleopteran insects. In particular, interfering RNA molecules that capable of interfering with pest histone genes and that are toxic to the target pest are provided. Further, methods of making and using the interfering RNA, for example in transgenic plants to confer protection from insect damage are disclosed.

17 Claims, 2 Drawing Sheets

Specification includes a Sequence Listing.

```
Dun_H2B_CDS    ATGCCTCCTAAGACTAGTGGTAAAGCTGCTAAAAAAGCAGGAAAAGCTCAGAAGAATATT
Dvi_H2B_CDS    ATGCCTCCTAAGACGAGTGGTAAAGCTGCTAAAAAAGCAGGGAAAGCCCAGAAGAACATT
Dba_H2B_CDS    ATGCCTCCTAAGACGAGTGGTAAAGCTGCTAAAAAGGCAGGAAAAGCCCAGAAGAACATT
               ************* ******************** ***** ***** ******** ***

Dun_H2B_CDS    TCCAAGACCGATAAGAAAAAGAAGCGTAAGAGGAAGGAAAGTTATGCCATTTACATCTAT
Dvi_H2B_CDS    TCAAAAACCGATAAGAAAAAGAAGCGAAAGAGGAAGGAAAGYTATGCTATTTACATTTAT
Dba_H2B_CDS    TCAAAAACCGATAAGAAAAAGAAGCGAAAGAGGAAGGAAAGCTATGCTATTTACATTTAT
               ** ** ******************** ************* ***** ******** ***

Dun_H2B_CDS    AAAGTATTGAAACAAGTGCATCCTGATACTGGTATTTCCAGTAAGGCTATGAGTATCATG
Dvi_H2B_CDS    AAAGTACTCAAACAAGTGCATCCTGATACCGGTATTTCCAGTAAGGCTATGAGTATCATG
Dba_H2B_CDS    AAAGTACTCAAACAAGTGCATCCTGATACCGGTATTTCCAGTAAGGCTATGAGTATCATG
               ****** * ******************** ******************************

Dun_H2B_CDS    AACAGTTTTGTAAATGATATTTTTGAAAGAATTGCTGCTGAAGCTTCTCGTTTAGCTCAT
Dvi_H2B_CDS    AACAGTTTTGTAAATGATATTTTTGAAAGAATCGCAGCTGAAGCTTCTCGTTTAGCTCAT
Dba_H2B_CDS    AACAGTTTTGTAAATGATATTTTTGAAAGAATCGCTGCCGAAGCTTCCCGTTTAGCTCAT
               ********************************  ** ** *******  *********** ************

Dun_H2B_CDS    TACAATAAACGGTCAACAATTACAAGCAGAGAAATTCAAACCGCCGTACGTTTATTACTT
Dvi_H2B_CDS    TATAATAAACGTTCTACAATTACAAGCAGAGAAATTCAAACCGCAGTACGTTTATTACTT
Dba_H2B_CDS    TATAATAAACGTTCTACAATTACAAGCAGAGAAATTCAAACGGCCGTACGTTTATTACTT
               ** ******** ** ************************** ** **************

Dun_H2B_CDS    CCTGGAGAGTTAGCTAAACACGCCGTTAGTGAAGGTACCAAAGCTGTTACTAAATATACA
Dvi_H2B_CDS    CCTGGAGAATTAGCTAAACACGCTGTCAGTGAAGGTACCAAAGCTGTTACTAAATACACA
Dba_H2B_CDS    CCTGGAGAATTAGCTAAACACGCTGTCAGTGAAGGCACCAAAGCTGTTACTAAATACACA
               ******* ************* ** ******** ****************** ***

Dun_H2B_CDS    AGTTCTAAG
Dvi_H2B_CDS    AGTTCTAAG
Dba_H2B_CDS    AGTTCTAAG
               *********
```

Fig. 1

```
Dun_H4_CDS_var2    ATGACTGGACGTGGAAAAGGTGGTAAAGGTTTGGGAAAAGGTGGCGCTAAACGTCATCGT
Dun_H4_CDS_var1    ATGACTGGACGTGGAAAAGGTGGTAAAGGTTTGGGAAAAGGTGGCGCTAAACGTCATCGT
Dvi_H4_CDS         ATGACTGGACGTGGAAAGGGTGGTAAAGGTTTGGGCAAAGGTGGCGCTAAACGTCACCGT
Dba_H4_CDS         ATGACTGGACGTGGAAAGGGTGGTAAAGGTTTGGGAAAAGGTGGCGCTAAACGTCACCGT
                   *****************  ******************* ******************  ***

Dun_H4_CDS_var2    AAAGTTTTGCGTGATAACATCCAAGGTATTACCAAGCCTGCTATCAGAAGATTGGCTCGT
Dun_H4_CDS_var1    AAAGTATTACGTGATAACATCCAAGGTATTACCAAGCCTGCTATCAGAAGACTAGCTCGT
Dvi_H4_CDS         AAAGTATTACGTGACAACATCCAAGGTATTACCAAGCCTGCTATAAGAAGATTAGCTCGT
Dba_H4_CDS         AAAGTGTTACGTGACAACATCCAAGGTATTACCAAGCCTGCTATAAGAAGATTAGCTCGT
                   ***** ** ***** ******************************  ****** * ******

Dun_H4_CDS_var2    CGAGGAGGAGTAAAACGTATTTCTGGCTTAATCTATGAGGAAACGAGAGGTGTATTGAAA
Dun_H4_CDS_var1    CGCGGAGGAGTAAAACGTATTTCTGGTTTAATCTATGAGGAAACGAGAGGTGTATTGAAA
Dvi_H4_CDS         CGCGGAGGTGTAAAACGTATCTCTGGTTTAATCTATGAGGAAACGCGAGGTGTATTGAAA
Dba_H4_CDS         CGCGGAGGTGTAAAACGTATCTCTGGTTTAATCTATGAGGAAACGCGAGGTGTATTGAAA
                   ** ***** *********** ***** ****************** **************

Dun_H4_CDS_var2    GTATTTTTGGAAAACGTTATTAGAGATGCTGTTACCTATACTGAACACGCCAAGAGGAAA
Dun_H4_CDS_var1    GTATTTTTGGAGAACGTCATTAGAGATGCAGTTACCTATACTGAGCACGCCAAAAGGAAA
Dvi_H4_CDS         GTATTTTTGGAAAACGTTATTAGAGATGCCGTTACCTATACTGAGCACGCCAAAAGGAAA
Dba_H4_CDS         GTATTTTTGGAAAACGTTATTAGAGATGCCGTTACCTATACTGAGCACGCCAAAAGGAAA
                   ***********  ***** ***********  *************** ******** ******

Dun_H4_CDS_var2    ACAGTAACTGCTATGGATGTTGTGTATGCACTTAAACGCCAAGGTCGTACTTTGTACGGT
Dun_H4_CDS_var1    ACAGTAACTGCTATGGATGTTGTATATGCACTTAAACGGCAAGGTCGTACGTTATATGGT
Dvi_H4_CDS         ACAGTAACTGCTATGGATGTTGTATATGCACTTAAACGACAAGGTCGTACTTTGTACGGT
Dba_H4_CDS         ACAGTAACTGCTATGGATGTTGTATATGCACTTAAACGACAAGGTCGTACTTTGTACGGT
                   *********************** ************** *********** ** ** ***

Dun_H4_CDS_var2    TTTGGTGGT
Dun_H4_CDS_var1    TTTGGTGGT
Dvi_H4_CDS         TTTGGTGGT
Dba_H4_CDS         TTTGGAGGT
                   ***** ***
```

BIOLOGICAL CONTROL OF COLEOPTERAN PESTS

RELATED APPLICATIONS

This application claims the benefit of provisional application 62/096,491 filed Dec. 23, 2014 and incorporated by reference in its entirety herein.

SEQUENCE LISTING

A substitute Sequence Listing in ASCII text format, submitted under 37 C.F.R. § 1.821, entitled "80291USPSP Seq Listing_ST25.txt", 39 kilobytes in size, generated on Apr. 17, 2018, and filed via EFS-Web is provided in lieu of a paper copy. This Sequence Listing is hereby incorporated by reference into the specification for its disclosures.

FIELD OF THE INVENTION

The invention relates generally to the control of pests that cause damage to crop plants by their feeding activities, and more particularly to the control of coleopteran pests by compositions comprising interfering RNA molecules. The invention further relates to the compositions and to methods of using such compositions comprising the interfering RNA molecules.

BACKGROUND

Insect species in the genus *Diabrotica* (corn rootworms and cucumber beetles) are considered some of the most important pests to crop plants. For example, species of corn rootworm, including *Diabrotica virgifera virgifera*, the western corn rootworm (WCR); *D. barberi*, the northern corn rootworm (NCR), *D. undecimpunctata howardi*, the southern corn rootworm (SCR), and *D. virgifera zeae*, the Mexican corn rootworm (MCR), are the most destructive corn pests in North America causing an estimated loss of over $1 billion annually. The western corn rootworm has also invaded Europe and causes an estimated 0.5 billion euros in damage each year. *Diabrotica speciosa* (common names include, among others, leaf beetle, little Brazilian beetle, cucurbit beetle and chrysanthemum beetle) is an important pest of corn, soybean and peanuts, in South America.

Most of the damage in corn is caused by larval rootworm feeding. Newly hatched rootworm larvae locate corn roots in the soil and initially begin feeding on the fine root hairs and burrow into root tips of the corn plant. As larvae grow larger, they feed on and tunnel into primary roots. When rootworms are abundant, larval feeding and deterioration of injured roots by root rot pathogens can result in roots being pruned to the base of the stalk. Severe root injury interferes with the roots' ability to transport water and nutrients into the plant, reduces plant growth, and results in reduced grain production. Severe root injury also may result in lodging of corn plants, making mechanical harvest more difficult or impossible. Corn rootworm adults feed primarily on corn silk, pollen, and kernels on exposed ear tips. If corn rootworm adults begin emerging before corn reproductive tissues are present, adults may feed on leaf tissue, scraping away the green surface tissue and leaving a window-pane appearance. Silk feeding by adults can result in pruning of silks at the ear tip, commonly called silk clipping. In field corn, beetle populations may reach a level high enough to cause severe silk clipping during pollen shed, which may interfere with pollination and reduce yield. Thus, unlike lepidopteran pests of corn in which only the larval stages cause damage, both the larval and adult stages of corn rootworm are capable of causing economic damage to corn.

*Diabrotica* insect pests are mainly controlled by intensive applications of chemical pesticides, which may be active against both larval and adult stages, through inhibition of insect growth, prevention of insect feeding or reproduction, or cause death. Good insect control can thus be reached, but these chemicals can sometimes also affect other, beneficial insects. Additional problems occur in areas of high insecticide use where populations of corn rootworm beetles have become resistant to certain insecticides. This has been partially alleviated by various resistance management practices, but there is an increasing need for alternative pest control agents.

Several native Cry proteins from *Bacillus thuringiensis*, or engineered Cry proteins, have been expressed in transgenic crop plants and exploited commercially to control certain lepidopteran and coleopteran insect pests. For example, starting in 2003, transgenic corn hybrids that control corn rootworm by expressing a Cry3Bb1, Cry34Ab1/Cry35Ab1 or modified Cry3A (mCry3A) or Cry3Ab (eCry3.1Ab) protein have been available commercially in the US.

The seed industry, university researchers and the US Environmental Protection Agency have worked together to develop management plans to help mitigate the onset of insect resistance to transgenic plants expressing insecticidal proteins. They are based primarily on a high dose and refuge strategy. A high dose strategy for corn is to use corn hybrids that express high enough levels of an insecticidal protein such as a Cry protein to kill even partially resistant insects. The underlying hypothesis is that killing partially resistant insects and preventing their mating greatly delays the development of resistance. The success of a high dose strategy depends in part on the specific activity of the insecticidal protein to the particular insect species and how much of that insecticidal protein can be expressed in the transgenic corn plant. The higher the specific activity of an insecticidal protein to a pest, the less amount of the insecticidal protein is required to be expressed in a transgenic plant to achieve a high dose strategy. For example, corn hybrids expressing the lepidopteran-active Cry protein, Cry1Ab, are considered high-dose against the primary target pest European corn borer (*Ostrinia nubilalis*). Because Cry1Ab is very toxic to European corn borer larvae with an LC50 <10 ng/cm$^2$ (i.e. high specific activity), levels of expression of Cry1Ab that are achievable in transgenic plants easily places such corn hybrids in a high dose category. However, unlike the lepidopteran-active products, current rootworm products are not considered high-dose. The proteins they express are not active against adults and have limited activity against late instar larvae. Therefore, the current transgenic rootworm products allow some rootworm larvae to survive and emerge as adults.

Thus, economic levels of silk clipping by corn rootworm adults may still occur even in portions of fields planted to a transgenic corn rootworm hybrid. For example, densities of western corn rootworm adults may exceed economic levels in portions of fields planted to transgenic corn rootworm hybrids due to immigration of beetles as well as direct emergence of adults from transgenic root systems. There have been many reports that confirm western corn rootworm adult emergence from certain corn transgenic rootworm hybrids (Crowder et al. (2005) J. Econ. Entomol. 98:534-551). Another publication suggests that western corn rootworm adults will exhibit similar feeding behaviors when encountering some transgenic corn plants or non-transgenic corn plants in the field and that it is unlikely that certain insecticidal proteins in transgenic plants will have significant effects on adults that might impact resistance management.

Therefore, identifying alternative insect control agents with new modes of action would be beneficial. Particularly useful would be new insect control agents that may be toxic to multiple life stages of the target insect pest. Such insect control agents may include those that target genetic elements, such as genes that are essential to the growth and survival of a target insect pest.

The organization of regulatory DNA elements into precise chromatin structures is important for both DNA replication and transcription in vivo (Lee et al. 1993. Cell 72:73-84; Felsenfeld (1992) Nature. 355:209). In eukaryotic cells, nuclear DNA exists as a hierarchy of chromatin structures, resulting in the compaction of nuclear DNA about 10,000 fold (Davie and Hendzel. 1994. J. Cell. Biochem. 55:98). The repeating structural unit in the extended 10 nm fiber form of chromatin is the nucleosome (van Holde. 1988. Chromatin. New York: Springer-Verlag). The nucleosome consists of 146 bp of DNA wrapped around a protein core of the histones H2A, H2B, H3, and H4, known as the core histones. These histones are arranged as an $(H3-H4)_2$ tetramer and two H2A-H2B dimmers positioned on each face of the tetramer. The DNA joining the nucleosomes is called linker DNA; it is to the linker DNA to which the H1 or linker histones bind. The 10 nm fiber is compacted further into the 30 nm fiber. Linker histones and amino-terminal regions ("tails") of the core histones maintain the higher order folding of chromatin (Garcia Ramirez et al. 1992. J. Biol Chem 267:19587). This chromatin structure must be relaxed when DNA is transcribed or translated. Thus, histones are critical to the proper processing of DNA for many living organisms, including insects.

Histone functionality is naturally modulated at the protein level by a number of mechanisms including methylation, which modulates transcriptional repression, and acetylation, which generally increases gene transcription. However, very few studies have reported the impact of modulating histones at the gene level by, for example, silencing genes encoding histone proteins using interfering RNA (RNAi) molecules. Boutros et al. (2004; Science 303:832-835) exposed *Drosophila* cells to double stranded RNA (dsRNA) molecules to test functionality of nearly all the genes in the *Drosophila* cell's genome, which included some histone genes. The phenotype that was scored was cell death. The results of this study indicate that dsRNA targeted to certain histone genes led to death of some cells in two *Drosophila* cell lines in vitro. However, the effect of targeting certain histone genes in those *Drosophila* cell lines was not as great as the positive control dsRNA targeted to an inhibitor of apoptosis (IAP) gene.

With the very limited number of studies and the variability of the results presented by Boutros et al., it is not clear that all histone genes are equally susceptible to silencing by RNAi in any given organism, particularly in certain insect species including coleopteran pest species like *Diabrotica* spp. It is also uncertain that histone genes in a pest *Diabrotica* species can be targeted as a pest control strategy. Furthermore, it is even more uncertain that the expression of such histone proteins can be modulated using interfering RNA molecules and that if such protein expression can be modulated, whether such modulation will result in toxicity to the target *Diabrotica* pest.

RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Most plant microRNAs (miRNAs) show extensive base pairing to, and guide cleavage of their target mRNAs (Jones-Rhoades et al. (2006) *Annu. Rev. Plant Biol.* 57, 19-53; Llave et al. (2002) *Proc. Natl. Acad. Sci. USA* 97, 13401-13406). In other instances, interfering RNAs may bind to target RNA molecules having imperfect complementarity, causing translational repression without mRNA degradation. The majority of the animal miRNAs studied so far appear to function in this manner.

There is an ongoing need for compositions and methods for using such compositions having insecticidal activity, for instance for use in crop protection or insect-mediated disease control. Novel compositions are required to overcome the problem of resistance to existing insecticides and/or to help mitigate the development of resistance to existing transgenic plant approaches. Ideally such compositions have a high toxicity and are effective when ingested orally by the target pest and have applicability for use against both the larval and adult stages of the pest insect. Thus any invention which provided compositions in which any of these properties was enhanced would represent a step forward in the art.

SUMMARY

The needs outlined above are met by the invention which, in various embodiments, provides new methods of controlling economically important insect pests. The invention in part comprises a method of inhibiting expression of one or more target genes and proteins in insect pests such as members of the genus *Diabrotica*. Specifically, the invention comprises methods of modulating expression of one or more histone genes in *Diabrotica* species such as *Diabrotica virgifera virgifera* (western corn rootworm), *Diabrotica barberi* (northern corn rootworm), *Diabrotica undecimpunctata howardi* (southern corn rootworm), *Diabrotica virgifera zeae* (Mexican corn rootworm), *Diabrotica speciosa* (chrysanthemum beetle), and related species, that causes cessation of feeding, growth, development and reproduction, and eventually results in the death of the insect. The method comprises introduction of an interfering RNA molecule comprising a double-stranded RNA (dsRNA) or its modified forms such as small interfering RNA (siRNA) sequences, into cells or into the extracellular environment, such as the midgut, within a pest insect body wherein the dsRNA or siRNA enters the cells and inhibits expression of at least one or more histone genes and wherein inhibition of the one or more histone genes exerts a deleterious effect upon the pest insect. It is specifically contemplated that the methods and compositions of the invention will be useful in limiting or eliminating pest insect infestation in or on any plant by providing one or more compositions comprising interfering RNA molecules comprising dsRNA or siRNA molecules in the diet of the pest. The invention also provides interfering RNA molecules that when delivered to an insect pest inhibits, through a toxic effect, the ability of the insect pest to survive, grow, feed and/or reproduce, or to limit pest related damage or loss to crop plants. Such delivery may be through production of the interfering RNA in a transgenic plant, for example corn, or by topically applying a composition comprising the interfering RNA to a plant or plant seed, such as a corn plant or corn seed. The interfering RNA molecule comprises a nucleotide sequence that is complementary to a nucleotide sequence of a mRNA transcribable from a histone gene or a portion of a nucleotide sequence of a mRNA transcribable from a histone gene of the pest insect and therefore inhibits expression of the histone gene, which causes cessation of feeding, growth, development, reproduction and eventually results in death of the pest insect. The invention is further drawn to nucleic acid constructs, nucleic acid molecules and recombinant vectors that comprise or encode at least a fragment of one strand of an interfering RNA molecule of the invention. The invention also provides chimeric nucleic acid molecules comprising an antisense strand of a dsRNA of the interfering RNA operably associated with a plant microRNA precursor molecule. The invention also provides artificial plant microRNA precursors comprising an antisense strand of a dsRNA of an interfering RNA of the invention.

The invention further provides an interfering ribonucleic acid (RNA) molecule wherein the RNA comprises at least one dsRNA wherein the dsRNA is a region of double-stranded RNA comprising annealed complementary strands, one strand of which comprises a sequence of at least 21 contiguous nucleotides which is at least partially complementary to a target nucleotide sequence within an *Diabrotica* spp histone target gene, and wherein the interfering RNA molecule (i) is at least 80% identical, at least 85% identical, at least 90% identical, at last 92% identical, at least 93% identical, at least 95% identical, at least 97% identical, at least 98% identical, or at least 99% identical to at least a 19 contiguous nucleotide fragment of SEQ ID NO: 2, SEQ ID NO: 6, SEQ ID NO: 28, SEQ ID NO: 32, SEQ ID NO: 37, SEQ ID NO: 42, or SEQ ID NO: 47, or the complement thereof; or (ii) comprises at least a 19 contiguous nucleotide fragment of SEQ ID NO: 2, SEQ ID NO: 6, SEQ ID NO: 28, SEQ ID NO: 32, SEQ ID NO: 37, SEQ ID NO: 42, or SEQ ID NO: 47, or the complement thereof; or (iii) comprises at least a 19 contiguous nucleotide fragment of a nucleotide sequence encoding an amino acid sequence encoded by SEQ ID NO: 2, SEQ ID NO: 6, SEQ ID NO: 28, SEQ ID NO: 32, SEQ ID NO: 37, SEQ ID NO: 42, or SEQ ID NO: 47, or the complement thereof, wherein the interfering RNA molecule down regulates the histone target gene in a target *Diabrotica* insect. In some embodiments, the interfering molecule may comprise at least two dsRNAs, wherein each dsRNA comprises a sequence of nucleotides which is at least partially complementary to a target nucleotide sequence within the histone target gene. In further embodiments, each of the dsRNAs may comprise a different sequence of nucleotides which is complementary to a different target nucleotide sequence within the histone target gene.

The invention further provides compositions comprising one or more interfering RNA molecules comprising two or more of dsRNA molecules, wherein the two or more RNA molecules each comprise a different antisense strand, or comprising two or more nucleic acid constructs or nucleic acid molecules or artificial plant microRNA precursors of the invention.

The invention further provides insecticidal compositions for inhibiting the expression of a *Diabrotica* insect histone gene that comprises a dsRNA of the invention and an agriculturally acceptable carrier. Inhibition of the expression of the *Diabrotica* histone gene leads to cessation of feeding and growth and ultimately results in the death of the *Diabrotica* insect.

The invention is further drawn to transgenic plants which produce one or more interfering RNA molecules of the invention that are self-protected from insect feeding damage and to methods of using the plants alone or in combination with other insect control strategies to confer maximal insect control capabilities. Plants and/or plant parts producing one or more interfering RNA molecules of the invention or treated with a composition comprising one or more interfering RNA molecules of the invention are highly resistant to insect pest infestation. For example, economically important coleopteran pests in the genus *Diabrotica* can be controlled by a plant that produces an interfering RNA molecule of the invention or by a plant or plant seed that is treated with a composition comprising an interfering RNA molecule of the invention.

The invention also provides a method of controlling a *Diabrotica* insect comprising contacting the *Diabrotica* insect with a nucleic acid molecule that is or is capable of producing an interfering RNA of the invention for inhibiting expression of a histone gene in the *Diabrotica* insect thereby controlling the *Diabrotica* insect.

In other aspects, the invention provides a method of reducing an adult *Diabrotica* insect population on a transgenic plant expressing a Cry protein, a hybrid Cry protein or modified Cry protein comprising expressing in the transgenic plant a nucleic acid molecule that is or is capable of producing an interfering RNA of the invention capable of inhibiting expression of an histone gene in an adult *Diabrotica* insect thereby reducing the adult *Diabrotica* insect population.

In other aspects, the invention provides a method of reducing resistance development in a *Diabrotica* insect population to an interfering RNA of the invention, the method comprising expressing in a transgenic plant fed upon by the *Diabrotica* insect population an interfering RNA of the invention that is capable of inhibiting expression of a histone gene in a larval and adult *Diabrotica* insect, thereby reducing resistance development in the *Diabrotica* insect population compared to a *Diabrotica* insect population exposed to an interfering RNA capable of inhibiting expression of an histone gene in only the larval stage or adult stage of a *Diabrotica* insect.

In other aspects, the invention provides a method of reducing the level of a target RNA transcribable from a histone gene in a *Diabrotica* insect comprising contacting the *Diabrotica* insect with a composition comprising an interfering RNA molecule of the invention, wherein the interfering RNA molecule reduces the level of the target RNA in a cell of the *Diabrotica* insect.

In still other aspects, the invention provides a method of conferring *Diabrotica* insect tolerance to a plant, or part thereof, comprising introducing into the plant, or part thereof, an interfering RNA molecule, a dsRNA molecule, a nucleic acid construct, a chimeric nucleic acid molecule, an artificial plant microRNA precursor molecule and/or a composition of the invention, thereby conferring to the plant or part thereof tolerance to the *Diabrotica* insect.

In further aspects, the invention provides a method of reducing root damage to a plant fed upon by a *Diabrotica* insect, comprising introducing into cells of the plant an interfering RNA molecule, a dsRNA, a nucleic acid molecule, a nucleic acid construct, a chimeric nucleic acid molecule, an artificial plant microRNA precursor molecule and/or a composition of the invention, thereby reducing root damage to the plant fed upon by a *Diabrotica* insect.

In other aspects, the invention provides a method of producing a transgenic plant cell having toxicity to a *Diabrotica* insect, comprising introducing into a plant cell an interfering RNA molecule, a dsRNA, a nucleic acid molecule, a nucleic acid construct, a chimeric nucleic acid molecule, an artificial plant microRNA precursor molecule and/or a composition of the invention, thereby producing the transgenic plant cell having toxicity to the *Diabrotica* insect compared to a control plant cell.

In further aspects, the invention provides a method of producing a transgenic plant having enhanced tolerance to *Diabrotica* insect feeding damage, comprising introducing into a plant an interfering RNA molecule, a dsRNA, a nucleic acid molecule, a nucleic acid construct, a chimeric nucleic acid molecule, an artificial plant microRNA precursor molecule and/or a composition of the invention, thereby producing a transgenic plant having enhanced tolerance to *Diabrotica* insect feeding damage compared to a control plant.

In other aspects, the invention provides a method of enhancing control of a *Diabrotica* insect population comprising providing a transgenic plant or transgenic seed of the invention and applying to the transgenic plant or the transgenic seed a chemical pesticide that is insecticidal to a *Diabrotica* insect, thereby enhancing control of the *Diabrotica* insect population.

In other aspects, the invention provides a method of providing a corn grower with a means of controlling a *Diabrotica* insect pest population below an economic threshold in a corn crop comprising (a) selling or providing to the grower transgenic corn seed comprising a dsRNA, a nucleic acid molecule, a nucleic acid construct, a chimeric nucleic acid molecule, an artificial plant microRNA precursor molecule and/or a composition of the invention; and (b) advertising to the grower that the transgenic corn seed produces transgenic corn plants capable of controlling a *Diabrotica* insect pest population.

These and other aspects of the invention are set forth in more detail in the description of the invention below.

BRIEF DESCRIPTION OF THE DRAWINGS

FIG. 1 is an alignment of *Diabrotica* histone H2B coding sequences (CDS), where Dun H2B CDS is SEQ ID NO: 37, Dvi H2B CDS is SEQ ID NO: 6 and Dba H2B CDS is SEQ ID NO: 47. A "*" below a base (A, T, G or C) indicates an identical base as in the reference sequence. Bases that are different from the reference sequence are indicated by a ".". The alignment was created using methods similar to Edgar, 2004. (Nucleic Acids Res 32(5): 1792-97).

FIG. 2 is an alignment of *Diabrotica* histone H4 coding sequences (CDS), where Dun H4CDS var1 is SEQ ID NO: 28, Dun H4B CDS var2 is SEQ ID NO: 32, Dvi H4-CDS is SEQ ID NO: 2and Dba H4 CDS is SEQ ID NO: 42A "*" below a base (A, T, G or C) indicates an identical base as in the reference sequence. Bases that are different from the reference sequence are indicated by a ".". The alignment was created using methods similar to Edgar, 2004. (Nucleic Acids Res 32(5): 1792-97).

BRIEF DESCRIPTION OF THE SEQUENCES IN THE SEQUENCE LISTING

SEQ ID NO: 1 is a nucleotide sequence of a western corn rootworm histone H4 cDNA (DvH4) including the 5' and 3' untranslated regions (UTRs).

SEQ ID NO: 2 is a nucleotide sequence of the coding region of DvH4 comprised in SEQ ID NO:1.

SEQ ID NO: 3 is a sense strand nucleotide sequence of a mRNA transcribable from a DvH4 gene.

SEQ ID NO: 4 is an antisense sequence of the DvH4 mRNA designated DvH4*.

SEQ ID NO: 5 is a nucleotide sequence of a western corn rootworm histone H2B cDNA (DvH2B) including the 5' and 3' untranslated regions (UTRs).

SEQ ID NO: 6 is a nucleotide sequence of the coding region of DvH2B comprised in SEQ ID NO:5.

SEQ ID NO: 7 is a sense strand nucleotide sequence of a mRNA transcribable from a DvH2B gene.

SEQ ID NO: 8 is an antisense strand of the DvH2B mRNA designated DvH2B*.

SEQ ID NO: 9 is the DvH4 amino acid sequence encoded by SEQ ID NO:2.

SEQ ID NO: 10 is the DvH2B amino acid sequence encoded by SEQ ID NO:6.

SEQ ID NOs: 11-14 are examples of the 291 19-mer subsequences of DvH4 mRNA (SEQ ID NO:3) targetable by siRNA.

SEQ ID NOs: 15-18 are examples of the 351 19-mer subsequences of DvH2B mRNA (SEQ ID NO:7) targetable by siRNA.

SEQ ID NOs: 19-22 are examples of DvH4* anti-sense siRNA 19-mer sequences.

SEQ ID NOs: 23-26 are examples of DvH2B* anti-sense siRNA 19-mer sequences.

SEQ ID NO: 27 is variant 1 of a nucleotide sequence of a southern corn rootworm histone H4 cDNA (DuH4-1) including the 5' and 3' untranslated regions (UTRs).

SEQ ID NO: 28 is a nucleotide sequence of the coding region of DuH4-1 comprised in SEQ ID NO: 27.

SEQ ID NO: 29 is a sense strand nucleotide sequence of a mRNA transcribable from a DuH4 gene (DuH4-1 mRNA).

SEQ ID NO: 30 is an antisense sequence of the DuH4-1 mRNA designated DuH4-1*.

SEQ ID NO: 31 is variant 2 of a nucleotide sequence of a southern corn rootworm histone H4 cDNA (DuH4-2) including the 5' and 3' untranslated regions (UTRs).

SEQ ID NO: 32 is a nucleotide sequence of the coding region of DuH4-2 comprised in SEQ ID NO: 31.

SEQ ID NO: 33 is a sense strand nucleotide sequence of a mRNA transcribable from a DuH4 gene (DuH4-2 mRNA).

SEQ ID NO: 34 is an antisense strand of the DuH4 mRNA designated DuH4-2*.

SEQ ID NO: 35 is the DuH4 amino acid sequence encoded by SEQ ID NO: 28 and SEQ ID NO: 32.

SEQ ID NO: 36 is a nucleotide sequence of a southern corn rootworm histone H2B cDNA (DuH2B) including the 5' and 3' untranslated regions (UTRs).

SEQ ID NO: 37 is a nucleotide sequence of the coding region of DuH2B comprised in SEQ ID NO: 36.

SEQ ID NO: 38 is a sense strand nucleotide sequence of a mRNA transcribable from a DuH2B gene.

SEQ ID NO: 39 is an antisense sequence of the DuH2B mRNA designated DuH2B*.

SEQ ID NO: 40 is the DuH2B amino acid sequence encoded by SEQ ID NO: 37.

SEQ ID NO: 41 is a nucleotide sequence of a northern corn rootworm histone H4 cDNA (DbH4) including the 5' and 3' untranslated regions (UTRs).

SEQ ID NO: 42 is a nucleotide sequence of the coding region of DbH4 comprised in SEQ ID NO: 41.

SEQ ID NO: 43 is a sense strand nucleotide sequence of a mRNA transcribable from a DbH4 gene.

SEQ ID NO: 44 is an antisense sequence of the DbH4 mRNA designated DbH4*.

SEQ ID NO: 45 is the DbH4 amino acid sequence encoded by SEQ ID NO: 42.

SEQ ID NO: 46 is a nucleotide sequence of a northern corn rootworm histone H4 cDNA (DbH2B) including the 5' and 3' untranslated regions (UTRs).

SEQ ID NO: 47 is a nucleotide sequence of the coding region of DbH2B comprised in SEQ ID NO: 46.

SEQ ID NO: 48 is a sense strand nucleotide sequence of a mRNA transcribable from a DbH2B gene.

SEQ ID NO: 49 is an antisense sequence of the DbH2B mRNA designated DbH2B*.

SEQ ID NO: 50 is the DbH2B amino acid sequence encoded by SEQ ID NO: 47.

SEQ ID NO: 51-58 are primers useful to the invention.

SEQ ID NO: 59 is an expression cassette comprising the constitutive promoter prUbi1-18 (Christensen et al, 1992, PMB 18: 675), the terminator tZmUbi361-01 (U.S. Patent Application Publication No. US-2012-0198584), and capable of forming a dsRNA WCR H2B molecule comprising SEQ ID NO: 6 (DvH2B) and SEQ ID NO: 7 (DvH2B*), and intron AthBAF60-01.

SEQ ID NO: 60 is an expression cassette comprising the constitutive promoter prUbi1-18, the terminator tZmUbi361-01, and capable of forming a dsRNA WCR H4 molecule comprising SEQ ID NO: 3 (DvH4) and SEQ ID NO: 4 (DvH4*), and intron AthBAF60-01.

DETAILED DESCRIPTION

The following is a detailed description of the invention provided to aid those skilled in the art in practicing the invention. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments of the invention will be apparent to those skilled in the art in light of the instant disclosure, which do not depart from the invention. Hence, the following descriptions are intended to illustrate some particular embodiments of the invention, and not to exhaustively specify all permutations, combinations and variations thereof. Those of ordinary skill in the art will recognize that modifications and variations in the embodiments described herein may be made without departing from the spirit or scope of the invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

For clarity, certain terms used in the specification are defined and presented as follows:

As used herein, "a," "an" or "the" can mean one or more than one. For example, "a cell" can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

a. As used herein, "dsRNA" or "RNAi" refers to a polyribonucleotide structure formed either by a single self-complementary RNA strand or at least by two complementary RNA strands. The degree of complementary, in other words the % identity, need not necessarily be 100%. Rather, it must be sufficient to allow the formation of a double-stranded structure under the conditions employed. As used herein, the term "fully complementary" means that all the bases of the nucleotide sequence of the dsRNA are complementary to or 'match' the bases of the target nucleotide sequence. The term "at least partially complementary" means that there is less than a 100% match between the bases of the dsRNA and the bases of the target nucleotide sequence. The skilled person will understand that the dsRNA need only be at least partially complementary to the target nucleotide sequence in order to mediate down-regulation of expression of the target gene. It is known in the art that RNA sequences with insertions, deletions and mismatches relative to the target sequence can still be effective at RNAi. According to the current invention, it is preferred that the dsRNA and the target nucleotide sequence of the target gene share at least 80% or 85% sequence identity, preferably at least 90% or 95% sequence identity, or more preferably at least 97% or 98% sequence identity and still more preferably at least 99% sequence identity. Alternatively, the dsRNA may comprise 1, 2 or 3 mismatches as compared with the target nucleotide sequence over every length of 24 partially complementary nucleotides. It will be appreciated by the person skilled in the art that the degree of complementarity shared between the dsRNA and the target nucleotide sequence may vary depending on the target gene to be down-regulated or depending on the insect pest species in which gene expression is to be controlled.

b. It will be appreciated that the dsRNA may comprise or consist of a region of double-stranded RNA comprising annealed complementary strands, one strand of which, the sense strand, comprises a sequence of nucleotides at least partially complementary to a target nucleotide sequence within a target gene.

c. The target nucleotide sequence may be selected from any suitable region or nucleotide sequence of the target gene or RNA transcript thereof. For example, the target nucleotide sequence may be located within the 5'UTR or 3'UTR of the target gene or RNA transcript or within exonic or intronic regions of the gene. The skilled person will be aware of methods of identifying the most suitable target nucleotide sequences within the context of the full-length target gene. For example, multiple dsRNAs targeting different regions of the target gene can be synthesised and tested. Alternatively, digestion of the RNA transcript with enzymes such as RNAse H can be used to determine sites on the RNA that are in a conformation susceptible to gene silencing. Target sites may also be identified using in silico approaches, for example, the use of computer algorithms designed to predict the efficacy of gene silencing based on targeting different sites within the full-length gene.

Preferably, the % identity of a polyribonucleotide is determined by GAP (Needleman and Wunsch, 1970) analysis (GCG program) using the default settings, wherein the query sequence is at least about 21 to about 23 nucleotides in length, and the GAP analysis aligns the two sequences over a region of at least about 21 nucleotides. In another embodiment, the query sequence is at least 150 nucleotides in length, and the GAP analysis aligns the two sequences over a region of at least 150 nucleotides. In a further embodiment, the query sequence is at least 300 nucleotides in length and the GAP analysis aligns the two sequences over a region of at least 300 nucleotides. In yet another embodiment, the query sequence corresponds to the full length of the target RNA, for example mRNA, and the GAP analysis aligns the two sequences over the full length of the target RNA.

Conveniently, the dsRNA can be produced from a single open reading frame in a recombinant host cell, wherein the sense and anti-sense sequences are flanked by an unrelated sequence which enables the sense and anti-sense sequences to hybridize to form the dsRNA molecule with the unrelated sequence forming a loop structure. Alternatively, the sense strand and antisense strand can be made without an open reading frame to ensure that no protein will be made in the transgenic host cell. The two strands can also be expressed separately as two transcripts, one encoding the sense strand and one encoding the antisense strand.

RNA duplex formation can be initiated either inside or outside the cell. The dsRNA can be partially or fully double-stranded. The RNA can be enzymatically or chemically synthesized, either in vitro or in vivo.

The dsRNA need not be full length relative to either the primary transcription product or fully processed RNA. Generally, higher identity can be used to compensate for the use of a shorter sequence. Furthermore, the dsRNA can comprise single stranded regions as well, e.g., the dsRNA can be partially or fully double stranded. The double stranded region of the dsRNA can have a length of at least about 18 to about 25 base pairs, optionally a sequence of about 18 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs, up to a molecule that is double stranded for its full length, corresponding in size to a full length target RNA molecule.

The dsRNA can contain known nucleotide analogs or modified backbone residues or linkages, which are synthetic, naturally occurring, and non-naturally occurring. Examples of such analogs include, without limitation, phosphorothioates, phosphoramidates, methyl phosphonates, chiralmethyl phosphonates and 2-O-methyl ribonucleotides.

As used herein, the term "specifically reduce the level of a target RNA and/or the production of a target protein encoded by the RNA", and variations thereof, refers to the sequence of a portion of one strand of the dsRNA being sufficiently identical to the target RNA such that the presence of the dsRNA in a cell reduces the steady state level and/or the production of said RNA. In many instances, the target RNA will be mRNA, and the presence of the dsRNA in a cell producing the mRNA will result in a reduction in the production of said protein. Preferably, this accumulation or production is reduced at least 10%, more preferably at least 50%, even more preferably at least 75%, yet even more preferably at least 95% and most preferably 100%, when compared to a wild-type cell.

The consequences of inhibition can be confirmed by examination of the outward properties of the cell or organism or by biochemical techniques such as, but not limited to, Northern hybridization, reverse transcription, gene expression monitoring with a microarray, antibody binding, enzyme linked immunosorbent assay (ELISA), Western blotting, radioimmunoassay (RIA), and other immunoassays.

a. The interfering RNAs of the current invention may comprise one dsRNA or multiple dsRNAs, wherein each dsRNA comprises or consists of a sequence of nucleotides which is at least partially complementary to a target nucleotide sequence within the target histone gene and that functions upon uptake by an insect pest species to down-regulate expression of said target histone gene. Concatemeric RNA constructs of this type are described in WO2006/046148 as incorporated herein by reference. In the context of the present invention, the term 'multiple' means at least two, at least three, at least four, etc and up to at least 10, 15, 20 or at least 30. In one embodiment, the interfering RNA comprises multiple copies of a single dsRNA i.e. repeats of a dsRNA that binds to a particular target nucleotide sequence within a specific target histone gene. In another embodiment, the dsRNAs within the interfering RNA comprise or consist of different sequences of nucleotides complementary to different target nucleotide sequences. It should be clear that combinations of multiple copies of the same dsRNA combined with dsRNAs binding to different target nucleotide sequences are within the scope of the current invention.

b. The dsRNAs may be arranged as one contiguous region of the interfering RNA or may be separated by the presence of linker sequences. The linker sequence may comprise a short random nucleotide sequence that is not complementary to any target nucleotide sequences or target genes. In one embodiment, the linker is a conditionally self-cleaving RNA sequence, preferably a pH-sensitive linker or a hydrophobic-sensitive linker. In one embodiment, the linker comprises a sequence of nucleotides equivalent to an intronic sequence. Linker sequences of the current invention may range in length from about 1 base pair to about 10000 base pairs, provided that the linker does not impair the ability of the interfering RNA to down-regulate the expression of target histone gene(s).

In addition to the dsRNA(s) and any linker sequences, the interfering RNA of the invention may comprise at least one additional polynucleotide sequence. In different embodiments of the invention, the additional sequence is chosen from (i) a sequence capable of protecting the interfering RNA against RNA processing, (ii) a sequence affecting the stability of the interfering RNA, (iii) a sequence allowing protein binding, for example to facilitate uptake of the interfering RNA by cells of the insect pest species, (iv) a sequence facilitating large-scale production of the interfering RNA, (v) a sequence which is an aptamer that binds to a receptor or to a molecule on the surface of the insect pest cells to facilitate uptake, or (v) a sequence that catalyses processing of the interfering RNA within the insect pest cells and thereby enhances the efficacy of the interfering RNA. Structures for enhancing the stability of RNA molecules are well known in the art and are described further in WO2006/046148 as incorporated herein by reference.

The interfering RNA may contain DNA bases, non-natural bases or non-natural backbone linkages or modifications of the sugar-phosphate backbone, for example to enhance stability during storage or enhance resistance to degradation by nucleases. Furthermore, the interfering RNA may be produced chemically or enzymatically by one skilled in the art through manual or automated reactions. Alternatively, the interfering RNA may be transcribed from a polynucleotide encoding the same. Thus, provided herein is an isolated polynucleotide encoding any of the interfering RNAs of the current invention.

MicroRNAs (miRNAs) are non-protein coding RNAs, generally of between about 18 to about 25 nucleotides in length (commonly about 20-24 nucleotides in length in plants). These miRNAs direct cleavage in trans of target transcripts, negatively regulating the expression of genes involved in various regulation and development pathways (Bartel, *Cell,* 116:281-297 (2004); Zhang et al. *Dev. Biol.* 289:3-16 (2006)). As such, miRNAs have been shown to be involved in different aspects of plant growth and development as well as in signal transduction and protein degradation. In addition, small endogenous mRNAs including miRNAs may also be involved in biotic stress responses such as pathogen attack. Since the first miRNAs were discovered in plants (Reinhart et al. *Genes Dev.* 16:1616-1626 (2002), Park et al. *Curr. Biol.* 12:1484-1495 (2002)) many hundreds have been identified. Furthermore, many plant miRNAs have been shown to be highly conserved across very divergent taxa. (Floyd et al. *Nature* 428:485-486 (2004); Zhang et al. *Plant J.* 46:243-259 (2006)). Many microRNA genes (MIR genes) have been identified and made publicly available in a database (miRBase; microrna.sanger.ac.uk/sequences). miRNAs are also described in U.S. Patent Publications 2005/0120415 and 2005/144669A1, the entire contents of which are incorporated by reference herein.

Genes encoding miRNAs yield primary miRNAs (termed a "pri-miRNA") of 70 to 300 bp in length that can form imperfect stemloop structures. A single pri-miRNA may contain from one to several miRNA precursors. In animals, pri-miRNAs are processed in the nucleus into shorter hairpin RNAs of about 65 nt (pre-miRNAs) by the RNaseIII enzyme Drosha and its cofactor DGCR8/Pasha. The pre-miRNA is then exported to the cytoplasm, where it is further processed by another RNaseIII enzyme, Dicer, releasing a miRNA/miRNA* duplex of about 22 nt in size. In contrast to animals, in plants, the processing of pri-miRNAs into mature miRNAs occurs entirely in the nucleus using a single RNaseIII enzyme, DCL1 (Dicer-like 1). (Zhu. *Proc. Natl. Acad. Sci.* 105:9851-9852 (2008)). Many reviews on microRNA biogenesis and function are available, for example, see, Bartel *Cell* 116:281-297 (2004), Murchison et al. *Curr. Opin. Cell Biol.* 16:223-229 (2004), Dugas et al. *Curr. Opin. Plant Biol.* 7:512-520 (2004) and Kim *Nature Rev. Mol. Cell Biol.* 6:376-385 (2005).

The term "plant microRNA precursor molecule" as used herein describes a small (~70-300 nt) non-coding RNA sequence that is processed by plant enzymes to yield a ~19-24 nucleotide product known as a mature microRNA sequence. The mature sequences have regulatory roles through complementarity to messenger RNA (mRNA). The term "artificial plant microRNA precursor molecule" describes the non-coding miRNA precursor sequence prior to processing that is employed as a backbone sequence for the delivery of a siRNA molecule via substitution of the endogenous native miRNA/miRNA* duplex of the miRNA precursor molecule with that of a non-native, heterologous miRNA (amiRNA/amiRNA*; e.g. siRNA/siRNA*) that is then processed into the mature miRNA sequence with the siRNA sequence.

In the context of the invention, the term "toxic" used to describe a dsRNA of the invention means that the dsRNA molecules of the invention and combinations of such dsRNA molecules function as orally active insect control agents that have a negative effect on an insect. When a composition of the invention is delivered to the insect, the result is typically death of the insect, or the insect does not feed upon the source that makes the composition available to the insect. Such a composition may be a transgenic plant expressing the dsRNA of the invention.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

The terms "complementary" or "complementarity," as used herein, refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, the terms "substantially complementary" or "partially complementary" mean that two nucleic acid sequences are complementary at least about 50%, 60%, 70%, 80% or 90% of their nucleotides. In some embodiments, the two nucleic acid sequences can be complementary at least at 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art.

To "control" or "controlling" insects means to inhibit, through a toxic effect, the ability of one or more insect pests to survive, grow, feed, and/or reproduce, or to limit insect-related damage or loss in crop plants. To "control" insects may or may not mean killing the insects, although it preferably means killing the insects.

To "deliver" or "delivering" a composition or dsRNA means that the composition or dsRNA comes in contact with an insect, resulting in a toxic effect and control of the insect. The composition or dsRNA can be delivered in many recognized ways, e.g., orally by ingestion by the insect via transgenic plant expression, formulated composition(s), sprayable composition(s), a bait matrix, or any other art-recognized toxicant delivery system.

"*Diabrotica*" is a genus of beetles commonly referred to as "corn rootworms" or "cucumber beetles." *Diabrotica* insects that are pests of crop plants, include without limitation, *Diabrotica barberi* (northern corn rootworm; NCR), *D. virgifera virgifera* (western corn rootworm; WCR), *D. undecimpunctata howardii* (southern corn rootworm; SCR) and *D. virgifera zeae* (Mexican corn rootworm; MCR). In the context of the invention, the term "corn rootworm" or "cucumber beetle" is interchangeable with the term "*Diabrotica.*"

A "*Diabrotica* life stage" or "corn rootworm life stage" means the egg, larval, pupal or adult developmental form of a *Diabrotica* species.

"Effective insect-controlling amount" means that concentration of dsRNA that inhibits, through a toxic effect, the ability of insects to survive, grow, feed and/or reproduce, or to limit insect-related damage or loss in crop plants. "Effective insect-controlling amount" may or may not mean a concentration that kills the insects, although it preferably means that it kills the insects.

"Expression cassette" as used herein means a nucleic acid sequence capable of directing expression of a particular nucleic acid sequence in an appropriate host cell, comprising a promoter operably linked to the nucleic acid sequence of interest which is operably linked to termination signal sequences. It also typically comprises sequences required for proper translation of the nucleic acid sequence. The expression cassette comprising the nucleic acid sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleic acid sequence in the expression cassette may be under the control of, for example, a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding sequence, comprises other, primarily regulatory nucleic acid sequences responsible for the control of the expression, that is to say the transcription and translation, of the coding portion. A gene may also comprise other 5' and 3' untranslated sequences and termination sequences. Further elements that may be present are, for example, introns.

As used herein, the term "grower" means a person or entity that is engaged in agriculture, raising living organisms, such as crop plants, for example corn, for food, feed or raw materials.

A "heterologous" nucleic acid sequence is a nucleic acid sequence not naturally associated with a host cell into which it is introduced, including non-naturally occurring multiple copies of a naturally occurring nucleic acid sequence.

Histones are highly alkaline proteins found in eukaryotic cell nuclei that package and order the DNA into structural units called nucleosomes. They are the chief protein components of chromatin, and play a role in gene regulation. Histones H2A, H2B, H3, and H4 are the core histones, and form the nucleosome core, which comprises two H2A-H2B dimers and a H3-H4 tetramer. The four core histones are relatively similar in structure, and feature a main globular domain and a long N terminal tail. The core histones are subject to covalent modification, including acetylation and methylation, which may alter expression of genes located on DNA associated with its parent histone octamer.

A "homologous" nucleic acid sequence is a nucleic acid sequence naturally associated with a host cell into which it is introduced.

"Insecticidal" is defined as a toxic biological activity capable of controlling insects, preferably by killing them.

An "isolated" nucleic acid molecule or nucleotide sequence or nucleic acid construct or dsRNA molecule or protein of the invention is generally exists apart from its native environment and is therefore not a product of nature. An isolated nucleic acid molecule or nucleotide sequence or nucleic acid construct or dsRNA molecule or protein may exist in a purified form or may exist in a non-native environment such as, for example, a recombinant host or host cell such as a transgenic plant or transgenic plant cell.

In the context of the invention, a number in front of the suffix "mer" indicates a specified number of subunits. When applied to RNA or DNA, this specifies the number of bases in the molecule. For example, a 19 nucleotide subsequence of an mRNA having the sequence ACUGGUCGCGUUG-CAUGCU (SEQ ID NO: 61)is a "19-mer."

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A corn rootworm "transcriptome" is a collection of all or nearly all the ribonucleic acid (RNA) transcripts in a corn rootworm cell.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The nomenclature used herein for DNA or RNA bases and amino acids is as set forth in 37 C.F.R. § 1.822.

The invention is based on the unexpected discovery that double stranded RNA (dsRNA) or small interfering RNAs (siRNA) designed to target a mRNA transcribable from a histone gene of a *Diabrotica* insect are toxic to the *Diabrotica* insect pest and can be used to control *Diabrotica* infestation of a plant and impart to a transgenic plant tolerance to a *Diabrotica* infestation. Thus, in one embodiment, the invention provides a double stranded RNA (dsRNA) molecule comprising a sense strand and an antisense strand, wherein a nucleotide sequence of the antisense strand is complementary to a portion of a mRNA polynucleotide transcribable from a *Diabrotica* insect histone gene, wherein the dsRNA molecule is toxic to a *Diabrotica* insect.

In other embodiments, the invention provides an interfering RNA molecule comprising a dsRNA comprising a sense strand and an antisense strand, wherein a nucleotide sequence of the antisense strand is complementary to a portion of a mRNA polynucleotide transcribable from a *Diabrotica* histone gene that comprises a histone coding sequence having at least 90% identity, or at least 91% identity, or at least 92% identity, or at least 93% identity, or at least 94% identity, or at least 95% identity, or least 96% identity, or at least 97% identity, or at least 98% identity, or at least 99% identity to SEQ ID NO:2 (DvH4) or SEQ ID NO:6 (DvH2B), and wherein the dsRNA molecule is toxic to a *Diabrotica* insect. In some embodiments, the interfering ribonucleic acid (RNA) molecule comprises at least one dsRNA wherein the dsRNA is a region of double-stranded RNA comprising annealed complementary strands, one strand of which comprises a sequence of at least 19 contiguous nucleotides which is at least partially complementary to a target nucleotide sequence within an *Diabrotica* spp histone target gene, and wherein the interfering RNA molecule (i) is at least 85% identical to at least a 19 contiguous nucleotide fragment of SEQ ID NO: 2, SEQ ID NO: 6, SEQ ID NO: 28, SEQ ID NO: 32, SEQ ID NO: 37, SEQ ID NO: 42, or SEQ ID NO: 47, or the complement thereof; or (ii) comprises at least a 19 contiguous nucleotide fragment of SEQ ID NO: 2, SEQ ID NO: 6, SEQ ID NO: 28, SEQ ID NO: 32, SEQ ID NO: 37, SEQ ID NO: 42, or SEQ ID NO: 47, or the complement thereof; or (iii) comprises at least a 19 contiguous nucleotide fragment of a nucleotide sequence encoding an amino acid sequence encoded by SEQ ID NO: 2, SEQ ID NO: 6, SEQ ID NO: 28, SEQ ID NO: 32, SEQ ID NO: 37, SEQ ID NO: 42, or SEQ ID NO: 47, or the complement thereof, wherein the interfering RNA molecule down regulates the histone target gene in a target *Diabrotica* insect.

In some embodiments the *Diabrotica* histone target gene is from a *Diabrotica* insect selected from the group consisting of *Diabrotica barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle), *D. virgifera zeae* (Mexican corn rootworm), *D. beniensis, D. cristata, D. curvipustulata, D. dissimilis, D. elegantula, D. emorsitans, D. graminea, D. hispanolae, D. lemniscata, D. linsleyi, D. milleri, D. nummularis, D. occlusa, D. porracea, D. scutellata, D. tibialis, D. trifasciata* and *D. viridula*. In further embodiments, the *Diabrotica* insect is *D. virgifera virgifera* (western corn rootworm), *D. undecimpunctata howardi* (southern corn rootworm) or *D. barberi* (northen corn rootworm). In some embodiments, the histone gene is selected from the group consisting of an H1 histone, a H2A histone, a H2B histone, a H3 histone and an H4 histone. In some embodiments, the histone is an H4 or H2B histone. In some embodiments, the histone coding sequence comprises a sequence selected from the group comprising SEQ ID NO:2, SEQ ID NO:6, SEQ ID NO: 28, SEQ ID NO: 32, SEQ ID NO: 37, SEQ ID NO: 42, and SEQ ID NO: 47.

In some embodiments, the interfering RNA molecule comprises at least two dsRNAs, wherein each dsRNA comprises a sequence of nucleotides which is at least partially complementary to a target nucleotide sequence within the histone target gene. In some embodiments, each of the dsRNAs comprise a different sequence of nucleotides which is complementary to a different target nucleotide sequence within the histone target gene. In other embodiments, each of the dsRNAs comprise a different sequence of nucleotides which is complementary to a target nucleotide sequence within two different histone target genes.

In some embodiments, the interfering RNA molecule comprises a dsRNA that can comprise, consist essentially of or consist of from at least 18 to about 25 consecutive nucleotides (e.g. 18, 19, 20, 21, 22, 23, 24 or 25) to at least about 300 consecutive nucleotides. In some embodiments the dsRNA molecule can comprise, consist essentially of or consist of about 309, or about 369 consecutive nucleotides. Additional nucleotides can be added at the 3' end, the 5' end or both the 3' and 5' ends to facilitate manipulation of the dsRNA molecule but that do not materially affect the basic characteristics or function of the dsRNA molecule in RNA interference (RNAi).

In some embodiments, the interfering RNA molecule comprises a dsRNA which comprises an antisense strand that is complementary to comprises at least 18 consecutive nucleotides of SEQ ID NO:3, SEQ ID NO:7, SEQ ID NO: 29, SEQ ID NO: 33, SEQ ID NO: 38, SEQ ID NO: 43, or SEQ ID NO: 48. In other embodiments, the portion of dsRNA comprises, consists essentially of or consists of at least from 19, 20 or 21 consecutive nucleotides to at least about 300 consecutive nucleotides of SEQ ID NO:3, SEQ ID NO:7, SEQ ID NO: 29, SEQ ID NO: 33, SEQ ID NO: 38, SEQ ID NO: 43, or SEQ ID NO: 48. In other embodiments, the portion of dsRNA comprises, consists essentially of or consists of at least about 309 nucleotides of SEQ ID N0:3, at least about 369 consecutive nucleotides of SEQ ID NO: 7 at least about 309 nucleotides of SEQ ID NO: 29, at least about 309 nucleotides of SEQ ID NO: 33, at least about 369 consecutive nucleotides of SEQ ID NO: 38, at least about 309 nucleotides of SEQ ID NO: 43, or at least about 369 consecutive nucleotides of SEQ ID NO: 48.

In other embodiments, the interfering RNA molecule of the invention comprises a dsRNA which comprises, consists essentially of or consists of any 19-mer subsequence of SEQ ID NO:3 (DvH4 mRNA) consisting of N to N+18 nucleotides, wherein N is nucleotide 1 to 291 of SEQ ID NO:3. In other words, the portion of the mRNA that is targeted comprises, consists essentially of or consists of any of the 291 19 consecutive nucleotide subsequences (i.e. 19-mers) of SEQ ID NO:3, for example, bases 1-19 (5'-AUGACUG-GACGUGGAAAGG-3') (SEQ ID NO:11), bases 2-20 (5'-UGACUGGACGUGGAAAGGG-3') (SEQ ID NO:12), bases 3-21 (5'-GACUGGACGUGGAAAGGGU-3') (SEQ ID NO:13) and so forth to bases 291-309 (5'-UUUGUACG-GUUUUGGUGGU-3') (SEQ ID NO:14).

In other embodiments, the interfering RNA molecule of the invention comprises a dsRNA which comprises, consists essentially of or consists of any 19-mer subsequence of SEQ ID NO: 7 (DvH2B mRNA) consisting of N to N+18 nucleotides, wherein N is nucleotide 1 to nucleotide 351 of SEQ ID NO: 7. In other words, the portion of the mRNA that is targeted comprises any of the 351 19 consecutive nucleotide subsequences i.e. 19-mers) of SEQ ID NO: 7, for example bases 1-19 (5'-AUGCCUCCUAAGACGAGUG-3') (SEQ ID NO:15), bases 2-20 (5'-UGCCUCCUAAGAC-GAGUGG-3') (SEQ ID NO:16), bases 3-21 (5'-GCCUC-CUAAGACGAGUGGU-3') (SEQ ID NO:17) and so forth to bases 351-369 (5'-UAAAUACACAAGUUCUAAG-3') (SEQ ID NO:18). In other embodiments, the interfering RNA molecule of the invention comprises a dsRNA which comprises, consists essentially of or consists of any 19-mer subsequence of SEQ ID NO: 29 (DuH4-1) consisting of N to N+18 nucleotides, wherein N is nucleotide 1 to 291 of SEQ ID NO: 29; or any 19-mer subsequence of SEQ ID NO: 33 (DuH4-2) consisting of N to N+18 nucleotides, wherein N is nucleotide 1 to nucleotide 291 of SEQ ID NO: 33; or any 19-mer subsequence of SEQ ID NO: 38 (DuH28) consisting of N to N+18 nucleotides, wherein N is nucleotide 1 to 351 of SEQ ID NO: 38; or any 19-mer subsequence of SEQ ID NO: 43 (DbH4) consisting of N to N+18 nucleotides, wherein N is nucleotide 1 to nucleotide 291 of SEQ ID NO: 43; or any 19-mer subsequence of SEQ ID NO: 48 (DbH2B) consisting of N to N+18 nucleotides, wherein N is nucleotide 1 to 351 of SEQ ID NO: 48.

In still other embodiments, the interfering RNA molecule of the invention comprises a dsRNA which comprises, consists essentially of or consists of SEQ ID NO: 3, SEQ ID NO:7, SEQ ID NO: 29, SEQ ID NO: 33, SEQ ID NO: 38, SEQ ID NO: 43, or SEQ ID NO: 48.

In further embodiments of the interfering RNA molecule of the invention, the nucleotide sequence of the antisense strand of the dsRNA can comprise, consist essentially of or consist of any 19-mer subsequence of SEQ ID NO:4 (DvH4*) consisting of N to N+18 nucleotides, wherein N is nucleotide 1 to 291 of SEQ ID NO:4. In other words, the antisense strand comprises, consists essentially of or consists of any of the 291 19 consecutive nucleotide subsequences (i.e. 19-mers) of SEQ ID NO:4, for example, bases 1-19 (5'-UACUGACCUGCACCUUUCC-3') (SEQ ID NO:19), bases 2-20 (5'-ACUGACCUGCACCUUUCCC-3') (SEQ ID NO:20), bases 3-21 (5'-CUGACCUGCAC-CUUUCCCA-3') (SEQ ID NO:21) and so forth to bases 291-309 (5'-AAACAUGCCAAAACCACCA-3') (SEQ ID NO:22).

In other embodiments of the interfering RNA molecule of the invention, the nucleotide sequence of the antisense strand of the dsRNA can comprise, consist essentially of or consist of any 19-mer subsequence of SEQ ID NO:8 (DvH2B*) consisting of N to N+18 nucleotides, wherein N is nucleotide 1 to nucleotide 351 of SEQ ID NO:8. In other words, the antisense strand consists essentially of any of the 351 19 consecutive nucleotide subsequences (i.e. 19-mer) of SEQ ID NO:8, for example, bases 1-19 (5'-UACGGAGGAUUCUGCUCAC-3') (SEQ ID NO:23), bases 2-20 (5'-ACGGAGGAUUCUGCUCACC-3') (SEQ ID NO:24), bases 3-21 (5'-CGGAGGAUUCUGCU-CACCA-3') (SEQ ID NO:25) and so forth to bases 351-369 (5'-UGAUUUAUGUGUUCAAGAU-3') (SEQ ID NO:26).

In other embodiments of the interfering RNA molecule of the invention, the nucleotide sequence of the antisense strand of the dsRNA can comprise, consist essentially of or consist of any 19-mer subsequence of SEQ ID NO: 30 (DuH4-11 consisting of N to N+18 nucleotides, wherein N is nucleotide 1 to 291 of SEQ ID NO: 30; or any 19-mer subsequence of SEQ ID NO: 34 (DuH4-21 consisting of N to N+18 nucleotides, wherein N is nucleotide 1 to nucleotide 291 of SEQ ID NO: 34; or any 19-mer subsequence of SEQ ID NO: 39 (DuH2B*) consisting of N to N+18 nucleotides, wherein N is nucleotide 1 to 351 of SEQ ID NO: 39; or any 19-mer subsequence of SEQ ID NO: 44 (DbH4*) consisting of N to N+18 nucleotides, wherein N is nucleotide 1 to nucleotide 291 of SEQ ID NO: 44; or any 19-mer subsequence of SEQ ID NO: 49 (DbH2B*) consisting of N to N+18 nucleotides, wherein N is nucleotide 1 to 351 of SEQ ID NO: 49.

In still other embodiments, the nucleotide sequence of the antisense strand of a dsRNA of the invention that is complementary to a portion of a mRNA polynucleotide transcribable from a *Diabrotica* insect histone gene comprises, consists essentially of or consists of the nucleotide sequence of SEQ ID NO: 4, SEQ ID NO: 8, SEQ ID NO: 30, SEQ ID NO: 34, SEQ ID NO: 39, SEQ ID NO: 44, or SEQ ID NO: 49. It is to be understood that any of the 19-mer sequences of SEQ ID NO: 4, SEQ ID NO: 8, SEQ ID NO: 30, SEQ ID NO: 34, SEQ ID NO: 39, SEQ ID NO: 44, or SEQ ID NO: 49 can have one nucleotide at either the 3' or 5' end deleted or can have up to six nucleotides added at the 3' end, the 5' end or both, in any combination to achieve an antisense strand consisting essentially of any 19-mer nucleotide sequence of SEQ ID NO: 4, SEQ ID NO: 8, SEQ ID NO: 30, SEQ ID NO: 34, SEQ ID NO: 39, SEQ ID NO: 44, or SEQ ID NO: 49, as it would be understood that the deletion of the one nucleotide or the addition of up to the six nucleotides do not materially affect the basic characteristics or function of the double stranded RNA molecule of the invention. Such additional nucleotides can be nucleotides that extend the complementarity of the antisense strand along the target sequence and/or such nucleotides can be nucleotides that facilitate manipulation of the RNA molecule or a nucleic acid molecule encoding the RNA molecule, as would be known to one of ordinary skill in the art. For example, a TT overhang at the 3' end may be present, which is used to stabilize the siRNA duplex and does not affect the specificity of the siRNA.

In some embodiments of this invention, the antisense strand of the double stranded RNA of the interfering RNA molecule can be fully complementary to the target RNA polynucleotide or the antisense strand can be substantially complementary or partially complementary to the target RNA polynucleotide. The dsRNA of the interfering RNA molecule may comprise a dsRNA which is a region of double-stranded RNA comprising substantially complementary annealed strands, or which is a region of double-stranded RNA comprising fully complementary annealed strands. By substantially or partially complementary is meant that the antisense strand and the target RNA polynucleotide can be mismatched at about 1, 2, 3, 4, 5, 6, 7, 8, 9, or 10 nucleotide pairings. Such mismatches can be introduced into the antisense strand sequence, e.g., near the 3' end, to enhance processing of the double stranded RNA molecule by Dicer, to duplicate a pattern of mismatches in a siRNA molecule inserted into a chimeric nucleic acid molecule or artificial microRNA precursor molecule of this invention (see Examples section), and the like, as would be known to one of skill in the art. Such modification will weaken the base pairing at one end of the duplex and generate strand asymmetry, therefore enhancing the chance of the antisense strand, instead of the sense strand, being processed and silencing the intended gene (Geng and Ding "Double-mismatched siRNAs enhance selective gene silencing of a mutant ALS-causing Allele1" *Acta Pharmacol. Sin.* 29:211-216 (2008); Schwarz et al. "Asymmetry in the assembly of the RNAi enzyme complex" *Cell* 115:199-208 (2003)).

In some embodiments of this invention, the interfering RNA comprises a dsRNA which comprises a short hairpin RNA (shRNA) molecule. Expression of shRNA in cells is typically accomplished by delivery of plasmids or recombinant vectors, for example in transgenic plants such as transgenic corn.

The invention encompasses a nucleic acid construct comprising an interfering RNA of the invention. The invention further encompasses a nucleic acid molecule encoding at least one interfering molecule of the invention. The invention further encompasses a nucleic acid construct comprising at least one interfering molecule of the invention or comprising a nucleic acid molecule encoding the at least interfering molecule of the invention. The invention further encompasses a nucleic acid construct wherein the nucleic acid construct is an expression vector. The invention further encompasses a recombinant vector comprising a regulatory sequence operably linked to a nucleotide sequence that encodes an interfering RNA molecule of the invention. A regulatory sequence may refer to a promoter, enhancer, transcription factor binding site, insulator, silencer, or any other DNA element involved in the expression of a gene.

The invention further encompasses chimeric nucleic acid molecules comprising an interfering RNA molecule with an antisense strand of a dsRNA operably linked with a plant microRNA precursor molecule. In some embodiments, the chimeric nucleic acid molecule comprises an antisense strand having the nucleotide sequence of any of the 19-mer subsequences of SEQ ID NO:4 or SEQ ID NO:8 operably linked with a plant microRNA precursor molecule. In some embodiments, the plant microRNA precursor molecule is a maize microRNA precursor.

In some embodiments, the invention encompasses an artificial plant microRNA precursor molecule comprising an antisense strand of a dsRNA of an interfering RNA molecule of the invention. In other embodiments, the artificial plant microRNA precursor molecule comprises an antisense strand having the nucleotide sequence of any of the 19-mer subsequences of SEQ ID NO:4 or SEQ ID NO:8. The use of artificial plant microRNAs to deliver a nucleotide sequence of interest (e.g an artificial miRNA; siRNA/siRNA*) into a plant is known in the art (see, e.g., Schwab et al. 2006. The Plant Cell 18:1121-1133 and Examples section herein). In the invention, the artificial microRNAs are chimeric or hybrid molecules, having a plant microRNA precursor backbone and an insect siRNA sequence inserted therein. As would be understood by one of ordinary skill in the art, it is typically desirable to maintain mismatches that normally occur in the plant microRNA precursor sequence in any nucleotide sequence that is substituted into the plant microRNA precursor backbone. In still other embodiments, the artificial plant microRNA precursor comprises portions of a corn microRNA precursor molecule. Any corn microRNA (miRNA) precursor is suitable for the compositions and methods of the invention. Non-limiting examples include miR156, miR159, miR160, miR162, miR164, miR166, miR167, miR168, miR169, miR171, miR172, miR319, miR390, miR393, miR394, miR395, miR396, miR397, miR398, miR399, miR408, miR482, miR528, miR529, miR827, miR1432, as well as any other plant miRNA precursors now known or later identified.

In some embodiments, the invention encompasses interfering RNA molecules, nucleic acid constructs, nucleic acid molecules or recombinant vectors comprising at least one strand of a dsRNA of an interfering RNA molecule of the invention, or comprising a chimeric nucleic acid molecule of the invention, or comprising an artificial plant microRNA of the invention. In some embodiments the nucleic acid construct comprises a nucleic acid molecule of the invention. In other embodiments, the nucleic acid construct is a recombinant expression vector.

In some embodiments, the invention encompasses compositions comprising an interfering RNA molecule comprising two or more dsRNAs, wherein the two or more dsRNAs each comprise a different antisense strand. In some embodiments the invention encompasses compositions comprising at least two more interfering RNA molecules, wherein the two or more interfering RNA molecules each comprise a dsRNA comprising a different antisense strand. The two or more interfering RNAs may be present on the same nucleic acid construct, on different nucleic acid constructs or any combination thereof. In other embodiments, the composition comprises RNA molecule comprising an antisense strand consisting essentially of the nucleotide sequence of SEQ ID NO: 4 and/or an RNA molecule comprising an antisense strand consisting essentially of the nucleotide sequence of SEQ ID NO: 8 and/or an RNA molecule comprising an antisense strand consisting essentially of the nucleotide sequence of SEQ ID NO: 30 and/or an RNA molecule comprising an antisense strand consisting essentially of the nucleotide sequence of SEQ ID NO: 34 and/or an RNA molecule comprising an antisense strand consisting essentially of the nucleotide sequence of SEQ ID NO: 39 and/or an RNA molecule comprising an antisense strand consisting essentially of the nucleotide sequence of SEQ ID NO: 44 and/or an RNA molecule comprising an antisense strand consisting essentially of the nucleotide sequence of SEQ ID NO: 49. In other embodiments, the composition may comprise two or more of the nucleic acid molecules, wherein the two or more nucleic acid molecules each encode a different interfering RNA molecule. In other embodiments, the composition may comprise two or more of the nucleic acid constructs, wherein the two or more nucleic acid constructs each comprise a nucleic acid molecule encoding a different interfering RNA.

In other embodiments, the composition comprises two or more nucleic acid constructs, two or more nucleic acid molecules, two or more chimeric nucleic acid molecules, two or more artificial plant microRNA precursors of the invention, wherein the two or more nucleic acid constructs, two or more nucleic acid molecules, two or more chimeric nucleic acid molecules, or two or more artificial plant microRNA precursors, each comprise a different antisense strand.

In some embodiments, the invention encompasses an insecticidal composition for inhibiting the expression of a *Diabrotica* insect histone gene, comprising an interfering RNA of the invention and an agriculturally acceptable carrier. In some embodiments, the acceptable agricultural carrier is a transgenic organism expressing an interfering RNA of the invention. In some embodiments the transgenic organism may be a transgenic plant expressing the interfering RNA of the invention that when fed upon by a target pest causes the target pest to stop feeding, growing or reproducing or causing death of the target pest. In other embodiments, the transgenic plant is a transgenic corn plant and the target pest is a *Diabrotica* insect pest. In still other embodiments, the *Diabrotica* insect pest is selected from the group consisting of *Diabrotica barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle), *D. virgifera zeae* (Mexican corn rootworm).

In other embodiments, the transgenic organism is selected from, but not limited to, the group consisting of: yeast, fungi, algae, bacteria, virus or an arthropod expressing the interfering RNA molecule of the invention. In some embodiments, the transgenic organism is a virus, for example an insect baculovirus that expresses an interfering RNA molecule of the invention upon infection of an insect host. Such a baculovirus is likely more virulent against the target insect than the wildtype untransformed baculovirus. In other embodiments the transgenic organism is a transgenic bacterium that is applied to an environment where a target pest occurs or is known to have occurred. In some embodiments, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive interfering RNA molecule for the same purpose.

In some embodiments, an acceptable agricultural carrier is a formulation useful for applying the composition comprising the interfering RNA molecule to a plant or seed. In some embodiments, the interfering RNA molecules are stabilized against degradation because of their double stranded nature and the introduction of Dnase/Rnase inhibitors. For example, dsRNA or siRNA can be stabilized by including thymidine or uridine nucleotide 3' overhangs. The dsRNA or siRNA contained in the compositions of the invention can be chemically synthesized at industrial scale in large amounts. Methods available would be through chemical synthesis or through the use of a biological agent.

In other embodiments the formulation comprises a transfection promoting agent. In other embodiments, the transfection promoting agent is a lipid-containing compound. In further embodiments, the lipid-containing compound is selected from the group consisting of; Lipofectamine, Cellfectin, DMRIE-C, DOTAP and Lipofectin. In another embodiment, the lipid-containing compound is a Tris cationic lipid.

In some embodiments, the formulation further comprises a nucleic acid condensing agent. The nucleic acid condensing agent can be any such compound known in the art. Examples of nucleic acid condensing agents include, but are not limited to, spermidine (N-[3-aminopropyl]-1,4-butanediamine), protamine sulphate, poly-lysine as well as other positively charged peptides. In some embodiments, the nucleic acid condensing agent is spermidine or protamine sulfate.

In still further embodiments, the formulation further comprises buffered sucrose or phosphate buffered saline.

In some embodiments, the invention encompasses transgenic plants, or parts thereof, comprising an interfering RNA molecule, a nucleic acid construct, a chimeric nucleic acid molecule, a artificial plant microRNA precursor molecule and/or a composition of the invention, wherein the transgenic plant has enhanced resistance to a *Diabrotica* insect as compared to a control plant. In other embodiments, the transgenic plant, or part thereof, is a transgenic corn plant, or part thereof. The invention further encompasses transgenic seed of the transgenic plants of the invention, wherein the transgenic seed comprises an interfering RNA molecule, a nucleic acid construct, a chimeric nucleic acid molecule, a artificial plant microRNA precursor molecule and/or a composition of the invention. In some embodiments the transgenic seed is a transgenic corn seed.

Transgenic plants expressing an interfering RNA of the invention are tolerant or resistant to attack by target insect pests. When the insect starts feeding on such a transgenic plant, it also ingests the expressed dsRNA or siRNA. This may deter the insect from further biting into the plant tissue or may even harm or kill the insect. A nucleic acid sequence encoding a dsRNA or siRNA of the invention is inserted into an expression cassette, which is then preferably stably integrated in the genome of the plant. The nucleic acid sequences of the expression cassette introduced into the genome of the plant are heterologous to the plant and non-naturally occurring. Plants transformed in accordance with the present invention may be monocots or dicots and include, but are not limited to, corn, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees. In further embodiments, the transgenic plant is a transgenic corn plant.

Expression of the interfering RNA molecule in transgenic plants is driven by regulatory sequences comprising promoters that function in plants. The choice of promoter will vary depending on the temporal and spatial requirements for expression, and also depending on the insect target species. Thus, expression of the interfering RNAs of this invention in leaves, in stalks or stems, in ears, in inflorescences (e.g. spikes, panicles, cobs, etc.), in roots, and/or seedlings is contemplated. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the dsRNA or siRNA in the desired cell.

Promoters useful with the invention include, but are not limited to, those that drive expression of a nucleotide sequence constitutively, those that drive expression when induced, and those that drive expression in a tissue- or developmentally-specific manner. These various types of promoters are known in the art.

Examples of constitutive promoters include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), figwort mosaic virus (fmv) promoter 1.5 (Govindarajulu et al. 2008. *Mol Plant Microbe Interact* 21:1027-35) and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in Quail et al. (U.S. Pat. No. 6,020,190).

In some embodiments, tissue-specific/tissue-preferred promoters can be used. Tissue-specific or tissue-preferred expression patterns include, but are not limited to, green tissue specific or preferred, root specific or preferred, stem specific or preferred, and flower specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in roots or particular cells in roots, pith, leaf or pollen. Such promoters are disclosed, for example without limitation, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; and the cestrum yellow leaf curling virus promoter disclosed in WO 01/73087, all incorporated herein by reference.

Additional examples of tissue-specific/tissue preferred promoters include, but are not limited to, the root hairspecific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology*, 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612). In some particular embodiments, the nucleotide sequences of the invention are operably associated with a root-preferred promoter. Particularly useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched on at the onset of senescence, such as the SAG promoter from *Arabidopsis* (Gan et al. (1995) *Science* 270:1986-1988).

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of nucleotide sequences of the invention in a plant through the application of an exogenous chemical regulator. Regulation of the expression of nucleotide sequences of the invention via promoters that are chemically regulated enables the polypeptides of the invention to be synthesized only when the crop plants are treated with the inducing chemicals. Depending upon the objective, the promoter may be a chemical-inducible promoter, where application of a chemical induces expression of a nucleotide sequence of the invention, or a chemical-repressible promoter, where application of the chemical represses expression of a nucleotide sequence of the invention.

Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid (e.g., the PR1a system), steroid steroid-responsive promoters (see, e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see, e.g., Gatz et al. (1991) *Mol. Gen. Genet.* 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters.

Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) *Current Opinion Biotechnol.* 7:168-172 and Gatz (1997) Annu. *Rev. Plant Physiol. Plant Mol. Biol.* 48:89-108. Other chemically inducible promoters useful for directing the expression of the nucleotide sequences of this invention in plants are disclosed in U.S. Pat. No. 5,614,395 herein incorporated by reference in its entirety. Chemical induction of gene expression is also detailed in the published application EP 0 332 104 (to Ciba-Geigy) and U.S. Pat. No. 5,614,395. In some embodiments, a promoter for chemical induction can be the tobacco PR-1a promoter.

In further aspects, the nucleotide sequences of the invention can be operably associated with a promoter that is wound inducible or inducible by pest or pathogen infection (e.g., a insect or nematode plant pest). Numerous promoters have been described which are expressed at wound sites and/or at the sites of pest attack (e.g., insect/nematode feeding) or phytopathogen infection. Ideally, such a promoter should be active only locally at or adjacent to the sites of attack, and in this way expression of the nucleotide sequences of the invention will be focused in the cells that are being invaded or fed upon. Such promoters include, but are not limited to, those described by Stanford et al., *Mol. Gen. Genet.* 215:200-208 (1989), Xu et al. *Plant Molec. Biol.* 22:573-588 (1993), Logemann et al. *Plant Cell* 1:151-158 (1989), Rohrmeier and Lehle, *Plant Molec. Biol.* 22:783-792 (1993), Firek et al. *Plant Molec. Biol.* 22:129-142 (1993), Warner et al. *Plant J.* 3:191-201 (1993), U.S. Pat. Nos. 5,750,386, 5,955,646, 6,262,344, 6,395,963, 6,703,541, 7,078,589, 7,196,247, 7,223,901, and U.S. Patent Application Publication 2010043102.

In some embodiments of the present invention, a "minimal promoter" or "basal promoter" is used. A minimal promoter is capable of recruiting and binding RNA polymerase II complex and its accessory proteins to permit transcriptional initiation and elongation. In some embodiments, a minimal promoter is constructed to comprise only the nucleotides/nucleotide sequences from a selected promoter that are required for binding of the transcription factors and transcription of a nucleotide sequence of interest that is operably associated with the minimal promoter including but not limited to TATA box sequences. In other embodiments, the minimal promoter lacks cis sequences that recruit and bind transcription factors that modulate (e.g., enhance, repress, confer tissue specificity, confer inducibility or repressibility) transcription. A minimal promoter is generally placed upstream (i.e., 5') of a nucleotide sequence to be expressed. Thus, nucleotides/nucleotide sequences from any promoter useable with the present invention can be selected for use as a minimal promoter.

In some embodiments, a recombinant nucleic acid molecule of the invention can be an "expression cassette." As used herein, "expression cassette" means a recombinant nucleic acid molecule comprising a nucleotide sequence of interest (e.g., the nucleotide sequences of the invention), wherein the nucleotide sequence is operably associated with at least a control sequence (e.g., a promoter). Thus, some embodiments of the invention provide expression cassettes designed to express nucleotides sequences encoding the dsRNAs or siRNAs of the invention. In this manner, for example, one or more plant promoters operably associated with one or more nucleotide sequences of the invention are provided in expression cassettes for expression in a corn plant, plant part and/or plant cell.

An expression cassette comprising a nucleotide sequence of interest may be chimeric, meaning that at least one of its components is heterologous with respect to at least one of its other components. An expression cassette may also be one that comprises a native promoter driving its native gene, however it has been obtained in a recombinant form useful for heterologous expression. Such usage of an expression cassette makes it so it is not naturally occurring in the cell into which it has been introduced.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used.

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) Biotech. 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of the invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac," pp. 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin, which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of the invention.

An expression cassette of the invention also can include polynucleotides that encode other desired traits. Such desired traits can be other polynucleotides which confer insect resistance, or which confer nematode resistance, or other agriculturally desirable traits. Such polynucleotides can be stacked with any combination of nucleotide sequences to create plants, plant parts or plant cells having the desired phenotype. Stacked combinations can be created by any method including, but not limited to, cross breeding plants by any conventional methodology, or by genetic transformation. If stacked by genetically transforming the plants, nucleotide sequences encoding additional desired traits can be combined at any time and in any order. For example, a single transgene can comprise multiple expression cassettes, such that multiple expression cassettes are introduced into the genome of a transformed cell at a single genomic location. Alternatively, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or other composition of the invention, provided by any combination of expression cassettes. For example, if two nucleotide sequences will be introduced, they can be incorporated in separate cassettes (trans) or can be incorporated on the same cassette (cis). Expression of the nucleotide sequences can be driven by the same promoter or by different promoters. It is further recognized that nucleotide sequences can be stacked at a desired genomic location using a site-specific recombination system. See, e.g., Int'l Patent Application Publication Nos. WO 99/25821; WO 99/25854; WO 99/25840; WO 99/25855 and WO 99/25853.

Thus, an expression cassette can include a coding sequence for one or more polypeptides for agronomic traits that primarily are of benefit to a seed company, grower or grain processor. A polypeptide of interest can be any polypeptide encoded by a polynucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, and/or fungal resistance. See, e.g., U.S. Pat. Nos. 5,569,823; 5,304,730; 5,495,071; 6,329,504; and 6,337,431.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construct of interest may be preferred. In the case of direct gene transfer, transformation with a single DNA species or co-transformation can be used (Schocher et al. Biotechnology 4:1093-1096 (1986)). For both direct gene transfer and *Agrobacterium*-mediated transfer, transformation is usually (but not necessarily) undertaken with a selectable marker that may provide resistance to an antibiotic (kanamycin, hygromycin or methotrexate) or a herbicide (basta). Plant transformation vectors of the invention may also comprise other selectable marker genes, for example, phosphomannose isomerase (pmi), which provides for positive selection of the transgenic plants as disclosed in U.S. Pat. Nos. 5,767,378 and 5,994,629, herein incorporated by reference, or phosphinotricin acetyltransferase (pat), which provides tolerance to the herbicide phosphinotricin (glufosinate). The choice of selectable marker is not, however, critical to the invention.

In other embodiments, a nucleic acid sequence of the invention is directly transformed into the plastid genome. Plastid transformation technology is extensively described in U.S. Pat. Nos. 5,451,513, 5,545,817, and 5,545,818, in PCT application no. WO 95/16783, and in McBride et al. (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Nati. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleic acid sequence of the present invention is inserted into a plastid-targeting vector and transformed into the plastid genome of a desired plant host. Plants homoplastic for plastid genomes containing a nucleic acid sequence of the present invention are obtained, and are preferentially capable of high expression of the nucleic acid sequence.

Transgenic plants or seed comprising an interfering RNA of the invention can also be treated with an insecticide or insecticidal seed coating as described in U.S. Pat. Nos. 5,849,320 and 5,876,739, herein incorporated by reference. Where both the insecticide or insecticidal seed coating and the transgenic plant or seed of the invention are active against the same target insect, for example a *Diabrotica* target pest, the combination is useful (i) in a method for further enhancing activity of the composition of the invention against the target insect, and (ii) in a method for preventing development of resistance to the composition of the invention by providing yet another mechanism of action against the target insect. Thus, the invention provides a method of enhancing control of a *Diabrotica* insect population comprising providing a transgenic plant or seed of the invention and applying to the plant or the seed an insecticide or insecticidal seed coating to a transgenic plant or seed of the invention. Examples of such insecticides and/or insecticidal seed coatings include, without limitation, a carbamate, a pyrethroid, an organophosphate, a friprole, a neonicotinoid, an organochloride, a nereistoxin, or a combination thereof. In another embodiment, the insecticide or insecticidal seed coating are selected from the group consisting of carbofuran, carbaryl, methomyl, bifenthrin, tefluthrin, permethrin, cyfluthrin, lambda-cyhalothrin, cypermethrin, deltamethrin, chlorpyrifos, chlorethoxyfos, dimethoate, ethoprophos, malathion, methyl-parathion, phorate, terbufos, tebupirimiphos, fipronil, acetamiprid, imidacloprid, thiacloprid, thiamethoxam, endosulfan, bensultap, and a combination thereof. Commercial products containing such insecticides and insecticidal seed coatings include, without limitation, Furadan®, Lanate®, Sevin®, Talstar®, Force®, Ammo®, Cymbush®, Delta Gold®, Karate®, Ambush®, Pounce®, Brigade®, Capture®, ProShield®, Warrior®, Dursban®, Fortress®, Mocap®, Thimet®, AAstar®, Rampart®, Counter®, Cygon®, Dicap®, Regent®, Cruiser®, Gaucho®, Prescribe®, Poncho® and Aztec®.

The compositions of the invention can also be combined with other biological control agents to enhance control of *Diabrotica* insect populations. Thus, the invention provides a method of enhancing control of a *Diabrotica* insect population by providing a transgenic plant that produces an interfering RNA of the invention and further comprises a polynucleotide that encodes a pesticidal agent, such as for example a patatin, a protease, an insecticidal protein, a bacterially-derived insecticidal protein, a *Bacillus thuringiensis* insecticidal protein, a *Xenorhabdus* insecticidal protein or protein complex, a *Photorhabdus* insecticidal protein or protein complex, a *Bacillus laterosporus* insecticidal protein or protein complex, and a *Bacillus sphaericus* insecticidal protein. In some embodiments, the *Bacillus thuringiensis* insecticidal protein is selected from the group consisting of a Cry1 protein, a Cry3 protein, a Cry 7 protein, a Cry8 protein, a Cry 23 protein, a Cry 36 protein, a Cry37 protein, a Cry34 protein together with a Cry35 protein, a modified Cry3A protein, and hybrid proteins made therefrom. In other embodiments, the *Bacillus thuringiensis* insecticidal protein is selected from the group consisting of Cry3Bb1, Cry34Ab1 together with Cry35Ab1, mCry3A and eCry3.1Ab. In another embodiment, the transgenic plant and transgenic seed is a corn plant or corn seed. In another embodiment, the transgenic corn plant is provided by crossing a first transgenic corn plant comprising a dsRNA of the invention with a transgenic corn plant comprising a transgenic event selected from the group consisting of MIR604, Event 5307, DAS51922-7, MON863 and MON88017.

Even where the insecticide or insecticidal seed coating is active against a different insect, the insecticide or insecticidal seed coating is useful to expand the range of insect control, for example by adding an insecticide or insecticidal seed coating that has activity against lepidopteran insects to the transgenic plant or seed of the invention, which has activity against coleopteran insects, the treated plant or coated transgenic seed controls both lepidopteran and coleopteran insect pests.

In further embodiments, the invention encompasses a biological sample from a transgenic plant, seed, or parts thereof, of the invention, wherein the sample comprises a nucleic acid that is or encodes at least one strand of a dsRNA of the invention. In other embodiments, the invention encompasses a commodity product derived from a transgenic plant, seed, or parts thereof, of the invention. In some embodiments, the commodity product is selected from the group consisting of whole or processed seeds, beans, grains, kernels, hulls, meals, grits, flours, sugars, sugars, starches, protein concentrates, protein isolates, waxes, oils, extracts, juices, concentrates, liquids, syrups, feed, silage, fiber, paper or other food or product produced from plants. In other embodiments, the biological sample or commodity product is toxic to insects. In other embodiments, the transgenic plant is transgenic corn plant.

The invention further encompasses a method of controlling a *Diabrotica* insect comprising contacting the *Diabrotica* insect with a nucleic acid molecule that is or is capable of producing an interfering RNA molecule of the invention for inhibiting expression of a histone gene in the *Diabrotica* insect thereby controlling the *Diabrotica* insect. In some embodiments, the histone gene comprises a histone coding sequence (i) having at least 80% identity, at least 85% identity, at least 90% identity, at least 95% identity, at least 96% identity, at least 97% identity, at least 98% identity, or at least 99% identity to at least a 19 contiguous nucleotide fragment of SEQ ID NO: 2, SEQ ID NO: 6, SEQ ID NO: 28, SEQ ID NO: 32, SEQ ID NO: 37, SEQ ID NO: 42, or SEQ ID NO: 47, or the complement thereof; or (ii) comprising at least a 19 contiguous nucleotide fragment of SEQ ID NO: 2, SEQ ID NO: 6, SEQ ID NO: 28, SEQ ID NO: 32, SEQ ID NO: 37, SEQ ID NO: 42, or SEQ ID NO: 47, or the complement thereof; or (iii) comprising at least a 19 contiguous nucleotide fragment of a nucleotide sequence encoding an amino acid sequence encoded by SEQ ID NO: 2, SEQ ID NO: 6, SEQ ID NO: 28, SEQ ID NO: 32, SEQ ID NO: 37, SEQ ID NO: 42, or SEQ ID NO: 47, or the complement thereof. In some embodiments the histone coding sequence comprises SEQ ID NO:2, SEQ ID NO:6, SEQ ID NO: 28, SEQ ID NO: 32, SEQ ID NO: 37, SEQ ID NO: 42, or SEQ ID NO: 47. In other embodiments, the interfering RNA molecule of the invention is complementary to a portion of a mRNA polynucleotide transcribable from the *Diabrotica* histone gene.

In some embodiments of the method of controlling a *Diabrotica* insect pest, the interfering RNA molecule comprises, consists essentially of or consists of from 18, 19, 20 or 21 consecutive nucleotides to at least about 300 consecutive nucleotides of SEQ ID NO:3, SEQ ID NO:7, SEQ ID NO: 29, SEQ ID NO: 33, SEQ ID NO: 38, SEQ ID NO: 43, or SEQ ID NO: 48. In other embodiments, the interfering RNA of the invention comprises, consists essentially of or consists of (a) any 19-mer subsequence of SEQ ID NO: 3 (DvH4 mRNA) consisting of N to N+18 nucleotides, wherein N is nucleotide 1 to 291 of SEQ ID NO: 3; (b) any 19-mer subsequence of SEQ ID NO: 7 (DvH2B mRNA) consisting of N to N+18 nucleotides, wherein N is nucleotide 1 to nucleotide 351 of SEQ ID NO: 7; (c) any 19-mer subsequence of SEQ ID NO: 29 (DuH4-1 mRNA) consisting of N to N+18 nucleotides, wherein N is nucleotide 1 to 291 of SEQ ID NO: 29; (d) any 19-mer subsequence of SEQ ID NO: 33 (DuH4-2 mRNA) consisting of N to N+18 nucleotides, wherein N is nucleotide 1 to nucleotide 291 of SEQ ID NO: 33; (e) any 19-mer subsequence of SEQ ID NO: 38 (DuH2B mRNA) consisting of N to N+18 nucleotides, wherein N is nucleotide 1 to nucleotide 351 of SEQ ID NO: 38; (f) any 19-mer subsequence of SEQ ID NO: 43 (DbH4 mRNA) consisting of N to N+18 nucleotides, wherein N is nucleotide 1 to nucleotide 291 of SEQ ID NO: 43; or (f) any 19-mer subsequence of SEQ ID NO: 48 (DbH2B mRNA) consisting of N to N+18 nucleotides, wherein N is nucleotide 1 to 351 of SEQ ID NO: 48. In other words, the method of controlling a *Diabrotica* insect pest, comprises an interfering RNA that comprises, consists essentially of or consists of any of the, for example, 291 19 consecutive nucleotide subsequences (i.e. 19-mers) of SEQ ID NO:3, for example, bases 1-19 (5'-AUGACUGGACGUGGAAAGG-3') (SEQ ID NO:11), bases 2-20 (5'-UGACUGGACGUG-GAAAGGG-3') (SEQ ID NO:12), bases 3-21 (5'-GACUG-GACGUGGAAAGGGU-3') (SEQ ID NO:13) and so forth to bases 291-309 (5'-UUUGUACGGUUUUGGUGGU-3') (SEQ ID NO:14). In other embodiments, the method of controlling a *Diabrotica* insect pest comprises an interfering RNA that comprises, consists essentially of or consists of any 19-mer subsequence of SEQ ID NO:7 (DvH2B mRNA) consisting of N to N+18 nucleotides, wherein N is nucleotide 1 to nucleotide 351 of SEQ ID NO:4. In other words, the portion of the mRNA that is targeted comprises, consists essentially of or consists of any of the 351 19 consecutive nucleotide subsequences (i.e. 19-mers) of SEQ ID NO: 7, for example bases 1-19 (5'-AUGCCUCCUAAGACGAGUG-3') (SEQ ID NO:15), bases 2-20 (5'-UGCCUCCUAAGAC-GAGUGG-3') (SEQ ID NO:16), bases 3-21 (5'-GCCUC-CUAAGACGAGUGGU-3') (SEQ ID NO:17) and so forth to bases 351-369 (5'-UAAAUACACAAGUUCUAAG-3') (SEQ ID NO:18). In still other embodiments, the method of controlling a *Diabrotica* insect pest, comprises an interfering RNA that the interfering RNA of the invention comprises, consists essentially of or consists of SEQ ID NO:3, SEQ ID NO:7, SEQ ID NO: 29, SEQ ID NO: 33, SEQ ID NO: 38, SEQ ID NO: 43, or SEQ ID NO: 48.

In some embodiments of the method of controlling a *Diabrotica* insect pest, the interfering RNA molecule, comprises, consists essentially of, or consists of (a) any 19-mer subsequence of SEQ ID NO:4 (DvH4*) consisting of N to N+18 nucleotides, wherein N is nucleotide 1 to 291 of SEQ ID NO:4; (b) any 19-mer subsequence of SEQ ID NO: 8 (DvH2B*) consisting of N to N+18 nucleotides, wherein N is nucleotide 1 to nucleotide 351 of SEQ ID NO:7; (c) any 19-mer subsequence of SEQ ID NO: 30 (DuH4-1*) consisting of N to N+18 nucleotides, wherein N is nucleotide 1 to 291 of SEQ ID NO: 30; (d) any 19-mer subsequence of SEQ ID NO: 34 (DuH4-2*) consisting of N to N+18 nucleotides, wherein N is nucleotide 1 to nucleotide 291 of SEQ ID NO: 34; (e) any 19-mer subsequence of SEQ ID NO: 39 (DuH2B*) consisting of N to N+18 nucleotides, wherein N is nucleotide 1 to nucleotide 351 of SEQ ID NO: 39; (f) any 19-mer subsequence of SEQ ID NO: 44 (DbH4*) consisting of N to N+18 nucleotides, wherein N is nucleotide 1 to nucleotide 291 of SEQ ID NO: 44; or (f) any 19-mer subsequence of SEQ ID NO: 49 (DbH2B*) consisting of N to N+18 nucleotides, wherein N is nucleotide 1 to 351 of SEQ ID NO: 49.

In other words, the method of controlling a *Diabrotica* insect pest, comprises an interfering RNA that comprises, consists essentially of or consists of, for example, any of the 291 19 consecutive nucleotide subsequences (i.e. 19-mers) of SEQ ID NO:4, for example, bases 1-19 (5'-UACUGAC-CUGCACCUUUCC-3') (SEQ ID NO:19), bases 2-20 (5'-ACUGACCUGCACCUUUCCC-3') (SEQ ID NO:20), bases 3-21 (5'-CUGACCUGCACCUUUCCCA-3') (SEQ ID NO:21) and so forth to bases 291-309 (5'-AAACAUGC-CAAAACCACCA-3') (SEQ ID NO:22). In other embodiments, the method of controlling a *Diabrotica* insect pest, comprises an interfering RNA that can comprise, consist essentially of or consist of the nucleotide sequence of any 19-mer subsequence of SEQ ID NO:8 (DvH2B*) consisting of N to N+18 nucleotides, wherein N is nucleotide 1 to nucleotide 351 of SEQ ID NO:8. In other words, the antisense strand comprises, consists essentially of or consists of any of the 351 19 consecutive nucleotide subsequences (i.e. 19-mers) of SEQ ID NO:8, for example, bases 1-19 (5'-UACGGAGGAUUCUGCUCAC-3') (SEQ ID NO:23), bases 2-20 (5'-ACGGAGGAUUCUGCUCACC-3') (SEQ ID NO:24), bases 3-21 (5'-CGGAGGAUUCUGCUCACCA-3') (SEQ ID NO:25) and so forth to bases 351-369 (5'-UGAUUUAUGUGUUCAAGAU-3') (SEQ ID NO:26). In other embodiments, the method of controlling a *Diabrotica* insect pest, comprises an interfering RNA that can comprise, consist essentially of or consist of the nucleotide sequence SEQ ID NO: 4, SEQ ID NO: 8, SEQ ID NO: 30, SEQ ID NO: 34, SEQ ID NO: 39, SEQ ID NO: 44, or SEQ ID NO: 49.

In some embodiments of the method of controlling a *Diabrotica* insect pest, the *Diabrotica* insect is selected from the group consisting of *D. barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle) and *D. virgifera zeae* (Mexican corn rootworm).

In other embodiments of the method of controlling the *Diabrotica* insect, the contacting comprises (a) planting a transgenic seed capable of producing a transgenic plant that expresses the nucleic acid molecule, wherein the *Diabrotica* insect feeds on the transgenic plant, or part thereof; or (b) applying a composition comprising the nucleic acid molecule to a seed or plant, or part thereof, wherein the *Diabrotica* insect feeds on the seed, the plant, or a part thereof. In some embodiments, the transgenic seed and the transgenic plant is a corn seed or a corn plant. In other embodiments the seed or plant is a corn seed or a corn plant.

The invention also encompasses a method of reducing an adult *Diabrotica* insect population on a transgenic plant expressing a Cry protein, a hybrid Cry protein or modified Cry protein comprising expressing in the transgenic plant a nucleic acid molecule that is or is capable of producing an interfering RNA capable of inhibiting expression of a histone gene in an adult *Diabrotica* insect thereby reducing the adult *Diabrotica* insect population.

In some embodiments, the invention encompasses a method of reducing the level of a target mRNA transcribable from a histone gene in a *Diabrotica* insect comprising contacting the *Diabrotica* insect with a composition comprising the interfering RNA molecule of the invention, wherein the interfering RNA molecule reduces the level of the target mRNA in a cell of the *Diabrotica* insect. In some embodiments, the interfering RNA of the method comprises at least one dsRNA wherein the dsRNA is a region of double-stranded RNA comprising annealed complementary strands, one strand of which comprises a sequence of at least 19 contiguous nucleotides which is at least partially complementary to a target nucleotide sequence within an *Diabrotica* spp histone target gene, and wherein the interfering RNA molecule (i) is at least 85% identical to at least a 19 contiguous nucleotide fragment of SEQ ID NO: 2, SEQ ID NO: 6, SEQ ID NO: 28, SEQ ID NO: 32, SEQ ID NO: 37, SEQ ID NO: 42, or SEQ ID NO: 47, or the complement thereof; or (ii) comprises at least a 19 contiguous nucleotide fragment of SEQ ID NO: 2, SEQ ID NO: 6, SEQ ID NO: 28, SEQ ID NO: 32, SEQ ID NO: 37, SEQ ID NO: 42, or SEQ ID NO: 47, or the complement thereof; or (iii) comprises at least a 19 contiguous nucleotide fragment of a nucleotide sequence encoding an amino acid sequence encoded by SEQ ID NO: 2, SEQ ID NO: 6, SEQ ID NO: 28, SEQ ID NO: 32, SEQ ID NO: 37, SEQ ID NO: 42, or SEQ ID NO: 47, or the complement thereof, wherein the interfering RNA molecule down regulates the histone target gene in a target *Diabrotica* insect. In another embodiment, the contacting is achieved by the *Diabrotica* insect feeding on the composition. In other embodiments, production of a histone protein encoded by the target mRNA is reduced. In other embodiments, the histone protein is a H4 histone or a H2B histone. In other embodiments, the histone protein comprises an amino acid having at least about 80%, at least about 85%, at least about 90%, at least about 91%, at least about 92%, at least about 93%, at least about 94%, at least about 95%, at least about 96%, at least about 97%, at least about 98% or at least about 99% identity to SEQ ID NO:9, SEQ ID NO:10, SEQ ID NO: 35, SEQ ID NO: 40, SEQ ID NO: 45, or SEQ ID NO: 50. In other embodiments the histone protein comprises SEQ ID NO:9 or SEQ ID NO:10. In other embodiments, the interfering RNA is contacted with a *Diabrotica* insect through a transgenic organism expressing the interfering RNA. In other embodiments, the transgenic organism is a transgenic plant, a transgenic bacterium or a transgenic endophyte. In other embodiments, the interfering RNA is contacted with a *Diabrotica* insect by topically applying an interfering RNA in an acceptable agricultural carrier to a plant or plant part on which the *Diabrotica* insects feeds. In some embodiments, the interfering RNA that reduces the level of a target mRNA transcribable from a histone gene in a *Diabrotica* insect is lethal to the *Diabrotica* insect. In some embodiments, the *Diabrotica* insect is selected from the group consisting of *D. barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle) and *D. virgifera zeae* (Mexican corn rootworm).

In some embodiments, the invention encompasses a method of conferring *Diabrotica* insect tolerance to a plant, or part thereof, comprising introducing into the plant, or part thereof, an interfering RNA molecule, a dsRNA molecule, a nucleic acid construct, a chimeric nucleic acid molecule, a artificial plant microRNA precursor molecule and/or a composition of the invention, wherein the dsRNA molecule, nucleic acid construct, chimeric nucleic acid molecule, artificial plant microRNA precursor molecule and/or composition of the invention are toxic to the *Diabrotica* insect, thereby conferring tolerance of the plant or part thereof to the *Diabrotica* insect. In other embodiments, the introducing step is performed by transforming a plant cell and producing the transgenic plant from the transformed plant cell. In still other embodiments, the introducing step is performed by breeding two plants together.

In other embodiments, the invention encompasses a method of reducing root damage to a plant fed upon by a *Diabrotica* insect, comprising introducing into cells of the plant an interfering RNA molecule, a dsRNA, a nucleic acid molecule, a nucleic acid construct, a chimeric nucleic acid molecule, an artificial plant microRNA precursor molecule and/or a composition of the invention, wherein the dsRNA, nucleic acid molecule, nucleic acid construct, chimeric nucleic acid molecule, artificial plant microRNA precursor molecule and/or composition of the invention are toxic to the *Diabrotica* insect, thereby reducing root damage to the plant. In other embodiments, the introducing step is performed by transforming a plant cell and producing the transgenic plant from the transformed plant cell. In still other embodiments, the introducing step is performed by breeding two plants together.

In still other embodiments, the invention encompasses a method of producing a transgenic plant cell having toxicity to a *Diabrotica* insect, comprising introducing into a plant cell an interfering RNA molecule, a dsRNA, a nucleic acid molecule, a nucleic acid construct, a chimeric nucleic acid molecule, an artificial plant microRNA precursor molecule and/or a composition of the invention, thereby producing the transgenic plant cell having toxicity to the *Diabrotica* insect compared to a control plant cell. In some embodiments, the invention encompasses a plurality of transgenic plant cells produced by this method. In other embodiments, the plurality of transgenic plant cells is grown under conditions which include natural sunlight. In other embodiments, the introducing step is performed by transforming a plant cell and producing the transgenic plant from the transformed plant cell. In still other embodiments, the introducing step is performed by breeding two plants together.

In some embodiments, the invention encompasses a method of producing a transgenic plant having enhanced tolerance to *Diabrotica* insect feeding damage, comprising introducing into a plant an interfering RNA molecule, a dsRNA, a nucleic acid molecule, a nucleic acid construct, a chimeric nucleic acid molecule, an artificial plant microRNA precursor molecule and/or a composition of the invention, thereby producing a transgenic plant having enhanced tolerance to *Diabrotica* insect feeding damage compared to a control plant. In other embodiments, the introducing step is performed by transforming a plant cell and producing the transgenic plant from the transformed plant cell. In still other embodiments, the introducing step is performed by breeding two plants together.

In some embodiments, the invention encompasses a method of providing a corn grower with a means of controlling a *Diabrotica* insect pest population in a corn crop comprising (a) selling or providing to the grower transgenic corn seed that comprises an interfering RNA, a nucleic acid molecule, a nucleic acid construct, a chimeric nucleic acid molecule, an artificial plant microRNA precursor molecule and/or a composition of the invention; and (b) advertising to the grower that the transgenic corn seed produce transgenic corn plants that control a *Diabrotica* pest population.

EXAMPLES

The invention will be further described by reference to the following detailed examples. These examples are provided for the purposes of illustration only, and are not intended to be limiting unless otherwise specified.

Example 1. Identification of Histone Genes in *Diabrotica virgifera virgifera*

This example describes the cloning and sequencing of histone genes and coding sequences from *Diabrotica* insects.

*Diabrotica virgifera virgifera* (Western Corn Rootworm; WCR) and *Diabrotica undecimpunctata howardi* (Southern Corn Rootworm; SCR) RNA Isolation Commercially-available WCR and SCR eggs were purchased (Crop Characteristics, Inc, Farmington, Minn.) and incubated at approximately 30° C. and ambient relative humidity. Newly emerged neonate SCR were collected (approximately 100-200) and total RNA was extracted with a PicoPure™ RNA Isolation Kit (Life Technologies, Carlsbad, Calif.) essentially according to the manufacturer's instructions. RNA concentration was measured by spectrophotometry and purity was assessed by absorbance ratios $A_{260/280}$ and $A_{260/230}$.

*Diabrotica barberi* (Northern Corn Rootworm; NCR) RNA Isolation

NCR eggs were obtained from the insect rearing facility at the USDA ARS NCARL (Brookings, S. Dak.) and incubated at about 30° C. and ambient relative humidity. Newly emerged neonates were collected (~20 total) and total RNA was extracted with a PicoPure™ RNA Isolation Kit (Life Technologies, Carlsbad, Calif.) essentially according to the manufacturer's instructions. RNA concentration was measured by spectrophotometry and purity was assessed by $A_{260/280}$ and $A_{260/230}$ ratios.

*Diabrotica virgifera virgifera* Pyrosequencing Library Preparation and Sequencing A whole-body neonate WCR transcriptome was sequenced by pyrosequencing on a 454 platform (454 Life Sciences, Branford, Conn.) essentially according to the manufacturer's instructions. The resulting reads (i.e., short fragments of nucleic acid sequence) were trimmed and assembled using a MIRA assembler (See, for example, Chevreux et al. 2004. Genome Res. 14:1147-1159, incorporated herein by reference).

*Diabrotica virgifera virgifera*, *D. undecimpunctata howardii* and *D. barberi* Illumina Library Preparation and Sequencing Whole-body neonate transcriptomes were sequenced on an Illumina Hi-Seq 2000 and the 100 bp paired-end library was constructed essentially according to the manufacturer's instructions. The resulting 2×100 Hi-Seq reads were retrieved and chunked for processing. The reads were assembled using ABySS version 1.3.5 on an MPI enabled SGE cluster. A k-mer sweep was performed for each sample to optimize the assemblies ranging from R to R/2 (where R is the read length, ~2 for step). The Unipaths from ABySS were retrieved for each k-mer and were de-redundified at 98% percent identity using Cd-Hit-Est version 4.6. The de-redundified unipath pool was processed using Cap3 with a 100 base overlap required. The resultant assemblies were de-redundified using Cd-Hit-Est. The data was then scaffolded using the abyss-scaffold program (independent of the ABySS workflow, but utilizing many of the tools). The assembly was finalized by gapclosing using SOAPdenovo GapCloser version 1.10. Reads were aligned to the final assembly using BWA to ensure good incorporation of read sequences and observe coverage profiles and pairing structures.

Identification of H2B and H4 Genes from *Diabrotica* Spp.

a. Assembled contiguous sequences (herein referred to as contigs) for each of the three *Diabrotica* species were compared via BLASTX (nucleotide translations searched against a protein database) to Uniprot Sprot, Uniprot Trembl, and Genbank NR databases. Contigs with matches to histone genes with an expect value of 1e-10 or lower were considered potentially significant matches. Full-length H2B and H4 genes are identified in each of the three species. The WCR H4 and H2B cDNA sequences are SEQ ID NO: 2 and SEQ ID NO: 6, respectively.

The WCR H2B and WCR H4 sequences were confirmed by Sanger sequencing (using standard methods) with forward and reverse primers to amplify the complete coding sequence of each gene (Table 1).

TABLE 1

Primers used to amplify the coding regions of WCR H2b and WCR H4.

| Primer Name | Sequence (5'→3') | Sequence Identifier |
|---|---|---|
| WCR_2B_FP01 | ATGCCTCCTAAGACGAGTGG | SEQ ID NO: 51 |
| WCR_H2B_RP01 | CTTAGAACTTGTGTATTTAG | SEQ ID NO: 52 |
| WCR_H4_FP02 | ATGACTGGACGTGGAAAGGG | SEQ ID NO: 53 |
| WCR_H4_RP02 | ACCACCAAAACCGTACAAAG | SEQ ID NO: 54 |

Example 2. Construction of Interfering RNA Molecules

This example describes the construction of interfering RNA molecules designed to target mRNA transcribable from *Diabrotica* histone genes.

Constructing WCR Histone H2b and Histone H4 dsRNA

The full length H2B and H4 genes were amplified from cDNA that was reverse transcribed using standard methods from mRNA isolated from whole body newly emerged neonates. Primers containing T7 promoter sequences (Table 2) were used to amplify the full length coding region of the genes followed by in vitro transcription, using standard methods, to synthesize dsRNA, also referred to as interfering RNA molecules. The RNA was purified by precipitation with equal volumes of 5 M ammonium acetate, followed by washing with at least 2 volumes of 70% ethanol and then resuspension of the dried RNA pellet with double distilled water.

TABLE 2

Primers used to amplify the coding regions of WCR H2b and WCR H4 and incorporate T7 promoter sequences to facilitate in vitro tanscription

| Primer Name | Sequence (5'→3') | Sequence Identifier |
|---|---|---|
| WCR_H2B_FP03 | TAATACGACTCACTATAGGGATG CCTCCTAAGACGAGTGG | SEQ. ID NO: 55 |
| WCR_H2B_RP03 | TAATACGACTCACTATAGGGCTT AGAACTTGTGTATTTAG | SEQ. ID NO: 56 |
| WCR_H4_FP04 | TAATACGACTCACTATAGGGATG ACTGGACGTGGAAAGGG | SEQ. ID NO: 57 |
| WCR_H4_RP04 | TAATACGACTCACTATAGGGACC ACCAAAACCGTACAAAG | SEQ. ID NO: 58 |

Example 3. Activity of dsRNA Against *Diabrotica virgifera*

This example describes testing interfering RNA molecules of the invention for biological activity against *Diabrotica virgifera*.

The interfering RNA molecules comprising dsRNA described above were tested for toxicity against *Diabrotica virgifera* in laboratory bioassays. Bioassays were performed using an RNA-treated artificial diet method. Briefly, molten artificial diet, modified from the diet of Marrone et al. 1985 (J. Econ. Entomol. 78:290-293), was poured into each well of 24-well plates and allowed to solidify. Interfering RNA molecules were diluted to appropriate concentration so that 60 μl of solution was added to the surface of the diet in each well, with a final overlay concentration of 100 ng dsRNA/cm$^2$. One *Diabrotica* larva was added to each well and each 24-well plate was maintained at approximately 28° C. and 16:8 light:dark photoperiod. Mortality was recorded at 9 and 12 d post-infestation. Interfering RNA molecules comprising dsRNA designed to target green florescent protein (GFP) was used in all bioassays as a negative control. The bioassay was repeated twice.

Interfering RNA molecules comprising double stranded RNAs designed to the complete coding sequence of *Diabrotica virgifera* H2B and H4 mRNA were tested against western corn rootworm larvae. The results, shown in Table 3, demonstrate that an interfering RNA molecule designed to target mRNA transcribable from a *Diabrotica* insect histone gene is highly toxic to *Diabrotica virgifera* (western corn rootworm). In these bioassays wcr histone2b/wcr histone2b* (SEQ ID NO: 7/SEQ ID NO: 8) and wcr histone4/wcr histone4* (SEQ ID NO: 3/SEQ ID NO: 4) produced 89 and 98% mortality, respectively, after 12 d.

TABLE 3

Activity of dsRNA against *Diabrotica virgifera* (western corn rootworm), 12 d after treatment

| dsRNA Treatment | Sample Size | | % WCR mortality | | |
|---|---|---|---|---|---|
| | Rep 1 | Rep 2 | Rep 1 | Rep 2 | Mean |
| wcr H2B/wcr H2B* | 24 | 23 | 87.5 | 91.3 | 89.4 |
| wcr H4/wcr H4* | 24 | 24 | 100 | 95.8 | 97.9 |

Example 4. Activity of Interfering RNA Molecules Against *Diabrotica undecimpunctata howardi*

This example describes testing interfering RNA molecules of the invention for biological activity against *Diabrotica undecimpunctata howardi*.

The interfering RNA molecules described above were tested for toxicity against *Diabrotica* undecimpunctata in laboratory bioassays. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. dsRNA molecules were diluted to appropriate concentration so that 20 μl of solution was added to the surface of the diet in each well, with a final overlay concentration series of 8 concentrations going from 0.5 μg/well down to 0.00022 μg/well in steps of 3× dilution. One *Diabrotica* larva was added to each well and each 48-well plate was maintained at approximately 25° C. and 16:8 light:dark photoperiod. Mortality was recorded at 1, 2, 3, 4, 5, 6, 7, 8, 9, 10, and 14 days post-infestation. dsRNA designed to target green fluorescent protein (GFP) was used in all bioassays as a negative control.

Interfering RNA molecules comprising double stranded RNAs designed to the coding sequence of *Diabrotica virgifera* H2B and H4 mRNA were tested against southern corn rootworm larvae. The results, shown in Table 4, demonstrate that an interfering RNA molecule comprising dsRNA designed to target mRNA transcribable from a *Diabrotica* insect histone gene is highly toxic to *Diabrotica undecimpunctata howardi* (southern corn rootworm). In these bioassays, wcr histone2b/wcr histone2b* (SEQ ID NO: 7/SEQ ID NO: 8) and wcr histone4/wcr histone4* (SEQ ID NO: 3/SEQ ID NO: 4) produced 69.7 and 84.8% mortality, respectively, after 14 d. The positive control was designed to target a highly expressed gene from southern corn rootworm. The $LT_{50}$ is the time (number of days) required to kill half the members of a tested population upon treatment. The $LC_{50}$ is the concentration (in μg/well) required to kill half the members of a tested population at day 14. Estimates of the $LT_{50}$ and $LC_{50}$ are obtained by curve analysis applied to data corrected with Abbott's formula.

TABLE 4

Activity of dsRNA against *Diabrotica undecimpunctata howardi* (southern corn rootworm), 14 d after treatment

| interfering RNA | % mortality @ day 14 | $LT_{50}$ @ 0.5 μg/well | $LC_{50}$ @ day 14 |
|---|---|---|---|
| GFP | 8.33 | NA | NA |
| scr positive control | 100.00 | 5.6 | 0.0209 |
| wcr histone2B | 72.22 | 12 | 0.0855 |
| wcr histone4 | 86.11 | 11.5 | 0.0444 |

Example 5. Expression of an Interfering RNA Molecule Comprising Histone dsRNA in Corn Plants This example describes introducing a construct that expresses an interfering RNA molecule into plant cells.

Vector Construction

Expression vectors designed to produce hairpin RNAs (hpRNA) consisted of a cassette containing a promoter, a sense strand, an intron functioning as a loop sequence, an antisense strand, and terminator. Two cassettes were designed to target either the WCR H2B or WCR H4 genes; one cassette (SEQ ID NO: 59) contained the sense and antisense strands to DvH2B (SEQ ID NO: 7) and DvH2B* (SEQ ID NO: 8). Another cassette (SEQ ID NO: 60) contained the sense and antisense strands to DvH4 (SEQ ID NO: 3) and DvH4* (SEQ ID NO: 4). The sense strand and antisense strand sequences were flanked by restriction endonuclease sites to facilitate cloning. The resulting expression cassettes (SEQ ID NO: 59 and SEQ ID NO: 60) were cloned separately into a binary vector suitable for plant transformation. Each complete binary vector contained a second cassette between the left and right borders, designed to express phosphomannose isomerase (pmi) as a selectable marker during plant transformation. The plasmid also contained selectable markers for selection in bacteria.

*Agrobacterium* Preparation

Each resulting plasmid containing the hairpin cassette was transformed into *Agrobacterium tumefaciens* using standard molecular biology techniques known to those skilled in the art. To prepare the Agrobacteria for transformation cells were cultured in liquid YPC media at 28° C. and 220 rpm overnight.

The vectors described above were transformed into maize. *Agrobacterium* transformation of immature maize embryos was performed essentially as described in Negrotto et al., 2000, Plant Cell Reports 19: 798-803. For this example, all media constituents are essentially as described in Negrotto et al., supra. However, various media constituents known in the art may be substituted.

Following transformation, selection, and regeneration, plants were tested for the presence of the pmi gene and the hairpin dsRNA interfering RNA molecule. Positive plants from the PCR assay were transferred to the greenhouse and tested for resistance to at least *Diabrotica virgifera* (western corn rootworm).

Whole Plant Assay

Corn plants growing in 4″ pots were infested with ~200 neonate corn rootworm larvae per plant. For each assay, 3 plants were used as uninfested controls. This included a single copy event representative of the infested test plants in the bioassay, a homozygous plant expressing a WCR protein trait (positive control), and negative control plant. These plants acted as controls for growth conditions during the course of the assay. Data were collected 10-14 days after infestation. Evaluations were primarily subjective measures comparing infested test plants to those of uninfested and infested control plants. One key visual evaluation that was made was whether the plants showed signs of lodging, a condition indicative of severe damage caused by extensive corn rootworm feeding on the root system. "+" indicates no apparent root damage; "−" indicates strong brace roots, some signs of feeding on secondary roots; "--" indicates lacking strong brace roots or lacking of secondary root growth, likely from feeding damage; '---' indicates significantly smaller root mass with likely root damage on at least 2-3 brace roots.

TABLE 5

Visual evaluations of transgenic corn infested with Western Corn Rootworm

| Plant | # events | + | − | -- | --- |
|---|---|---|---|---|---|
| no dsRNA | 2 | 0 | 0 | 0 | 2 |
| Histone2B dsRNA | 15 | 8 | 3 | 4 | 0 |
| Histone4 dsRNA | 15 | 7 | 5 | 3 | 0 |

The data in Table 5 indicate that the transgenic corn plants expressing dsRNAs that targeted genes encoding H2B or H4 suffered less root damage compared to the negative control plants.

It should be understood that the examples and embodiments described herein are for illustrative purposes only and that various modifications or changes in light thereof of the description will be suggested to persons skilled in the art and are to be included within the spirit and purview of this application and the scope of the appended claims.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

What is claimed is:

1. An interfering ribonucleic acid (RNA) molecule comprising at least one double-stranded RNA (dsRNA) comprising a sense strand and an anti-sense strand, wherein at least 21 consecutive nucleotides of the anti-sense strand is complementary to a portion of a mRNA polynucleotide transcribable from a *Diabrotica* histone H4 gene that comprises SEQ ID NO: 2, and wherein the dsRNA molecule is toxic to a *Diabrotica* insect.

2. The interfering RNA molecule of claim 1, wherein the sense strand comprises (a) any 21-mer subsequence of SEQ ID NO: 3 consisting of N to N+20 nucleotides, wherein N is nucleotide 1 to 289 of SEQ ID NO: 3.

3. The interfering RNA molecule of claim 1, wherein the anti-sense strand comprises (a) any 21-mer subsequence of SEQ ID NO: 4 consisting of N to N+20 nucleotides, wherein N is nucleotide 1 to 289 of SEQ ID NO: 4.

4. The interfering RNA molecule of claim 1, wherein (a) the sense strand comprises SEQ ID NO: 3; or (b) the anti-sense strand comprises SEQ ID NO: 4.

5. The interfering RNA molecule of claim 1, wherein the *Diabrotica* insect is selected from the group consisting of *D. barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle) and *D. virgifera zeae* (Mexican corn rootworm).

6. A nucleic acid construct comprising the interfering RNA molecule of claim 1.

7. A nucleic acid molecule encoding the interfering RNA molecule of claim 1.

8. The nucleic acid construct of claim 6 wherein the nucleic acid construct is an expression vector.

9. A recombinant vector comprising a regulatory sequence operably linked to a nucleotide sequence that encodes the interfering RNA molecule of claim 1.

10. A composition comprising two or more of the interfering RNA molecules of claim 1.

11. An insecticidal composition for inhibiting the expression of a *Diabrotica* insect histone gene, comprising the dsRNA of claim 1 and an agriculturally acceptable carrier.

12. A transgenic plant, or part thereof, comprising the interfering RNA molecule of claim 1, wherein the transgenic plant has enhanced resistance to a *Diabrotica* insect as compared to a control plant.

13. The transgenic plant, or part thereof, of claim 12, wherein the transgenic plant, or part thereof, is a maize plant or part thereof.

14. A transgenic seed comprising the nucleic acid construct of claim 8.

15. A biological sample from the transgenic plant, or part thereof, of claim 12.

16. A commodity product derived from the transgenic plant, or part thereof, of claim 12, wherein the commodity product comprises the interfering RNA molecule.

17. The commodity product of claim 16, wherein the commodity product is selected from the group consisting of whole or processed seeds, beans, grains, kernels, hulls, meals, grits, flours, sugars, sugars, starches, protein concentrates, protein isolates, waxes, oils, extracts, juices, concentrates, liquids, syrups, feed, silage, fiber, paper or other food or product produced from plants.

* * * * *

SEQUENCE LISTING

<160> NUMBER OF SEQ ID NOS: 61

<210> SEQ ID NO 1
<211> LENGTH: 399

```
<212> TYPE: DNA
<213> ORGANISM: Diabrotica virgifera

<400> SEQUENCE: 1
aattgagtaa ttccaggaca actgaactga ttgtaccatg actggacgtg gaaagggtgg      60
taaaggtttg ggcaaaggtg gcgctaaacg tcaccgtaaa gtattacgtg acaacatcca     120
aggtattacc aagcctgcta taagaagatt agctcgtcgc ggaggtgtaa acgtatctc      180 tggtttaatc tatgaggaaa cgcgaggtgt attgaaagta tttttggaaa cgttattag     240 agatgccgtt acctatactg agcacgccaa aggaaaaca gtaactgcta tggatgttgt      300
atatgcactt aaacgacaag gtcgtacttt gtacggtttt ggtggttaat tgctattaat    360
ttccatcctt aaaaaaaacg gttcttttca gaaccacgt                           399

<210> SEQ ID NO 2
<211> LENGTH: 309
<212> TYPE: DNA
<213> ORGANISM: Diabrotica virgifera

<400> SEQUENCE: 2
atgactggac gtggaaaggg tggtaaaggt ttgggcaaag gtggcgctaa acgtcaccgt      60
aaagtattac gtgacaacat ccaaggtatt accaagcctg ctataagaag attagctcgt    120
cgcggaggtg taaacgtat ctctggttta atctatgagg aaacgcgagg tgtattgaaa     180
gtattttggg aaaacgttat tagagatgcc gttacctata ctgagcacgc caaaaggaaa    240
acagtaactg ctatggatgt tgtatatgca cttaaacgac aaggtcgtac tttgtacggt    300
tttggtggt                                                             309

<210> SEQ ID NO 3
<211> LENGTH: 309
<212> TYPE: RNA
<213> ORGANISM: Diabrotica virgifera

<400> SEQUENCE: 3
augacuggac guggaaaggg ugguaaaggu uugggcaaag guggcgcuaa acgucaccgu      60
aaaguauuac gugacaacau ccaagguauu accaagccug cuauaagaag auuagcucgu    120
cgcggaggug uaaaacguau cucugguuua aucuaugagg aaacgcgagg uguauugaaa    180
guauuuuugg aaaacguuau uagagaugcc guuaccuaua cugagcacgc caaaaggaaa    240
acaguaacug cuauggaugu uguauaugca cuuaaacgac aaggucguac uuuguacggu    300
uuuggugg                                                              309

<210> SEQ ID NO 4
<211> LENGTH: 309
<212> TYPE: RNA
<213> ORGANISM: Artificial Sequence
<220> FEATURE:
<223> OTHER INFORMATION: Antisense strand of DvH4 mRNA

<400> SEQUENCE: 4
uacugaccug caccuuuccc accauuucca aacccguuuc caccgcgauu ugcaguggca      60
uuucauaaug cacuguugua gguuccauaa ugguucggac gauauucuuc uaacgagca     120 gcgccuccac auuuugcaua gagaccaaau uagauacucc uuugcgcucc acauaacuuu    180
cauaaaaacc uuuugcaaua aucucuacgg caauggauau gacucgugcg guuuuccuuu    240
ugucauugac gauaccuaca acauauacgu gaauuugcug uuccagcaug aaacauggca    300
``` aaaccacca                                                               309

<210> SEQ ID NO 5
<211> LENGTH: 478
<212> TYPE: DNA
<213> ORGANISM: Diabrotica virgifera

<400> SEQUENCE: 5
tcggggkagk tttcactttg attttcaaag agtaagcgtc attttgtttt tgcgatgcct      60
cctaagacga gtggtaaagc tgctaaaaaa gcagggaaag cccagaagaa catttcaaaa    120
accgataaga aaagaagcg aaagaggaag gaaagytatg ctatttacat ttataaagta     180
ctcaaacaag tgcatcctga taccggtatt tccagtaagg ctatgagtat catgaacagt    240
tttgtaaatg atattttga aagaatcgca gctgaagctt ctcgtttagc tcattataat    300
aaacgttcta caattacaag cagagaaatt caaaccgcag tacgtttatt acttcctgga    360
gaattagcta acacgctgt cagtgaaggt accaaagctg ttactaaata cacaagttct    420
aagtaatcaa gaabtttcat ctattaatta taacmaaacg gttcttttca gaaccaac     478

<210> SEQ ID NO 6
<211> LENGTH: 369
<212> TYPE: DNA
<213> ORGANISM: Diabrotica virgifera

<400> SEQUENCE: 6
atgcctccta agacgagtgg taaagctgct aaaaagcag ggaaagccca gaagaacatt      60 tcaaaaccg ataagaaaaa gaagcgaaag aggaaggaaa gytatgctat ttacattttat   120 aaagtactca acaagtgca tcctgatacc ggtatttcca gtaaggctat gagtatcatg    180
aacagttttg taaatgatat ttttgaaaga atcgcagctg aagcttctcg tttagctcat    240
tataataaac gttctacaat tacaagcaga gaaattcaaa ccgcagtacg tttattactt    300
cctggagaat tagctaaaca cgctgtcagt gaaggtacca aagctgttac taaatacaca    360
agttctaag                                                           369

<210> SEQ ID NO 7
<211> LENGTH: 369
<212> TYPE: RNA
<213> ORGANISM: Diabrotica virgifera

<400> SEQUENCE: 7
augccuccua agacgagugg uaaagcugcu aaaaagcag ggaaagccca gaagaacauu      60 ucaaaaccg auaagaaaaa gaagcgaaag aggaaggaaa gyuaugcuau uuacauuuau    120
aaaguacuca acaagugca uccugauacc gguauuucca guaaggcuau gaguaucaug    180
aacaguuuug uaaugauau uuugaaaga aucgcagcug aagcuucucg uuuagcucau    240
uauaauaaac guucuacaau uacaagcaga gaauucaaa ccgcaguacg uuuauuacuu    300
ccuggagaau uagcuaaaca cgcugucagu gaagguacca aagcuguuac uaauacaca    360 aguucuaag                                                           369

<210> SEQ ID NO 8
<211> LENGTH: 369
<212> TYPE: RNA
<213> ORGANISM: Artificial sequence
<220> FEATURE:
<223> OTHER INFORMATION: Antisense strand to DvH2B mRNA

<400> SEQUENCE: 8

```
uacggaggau ucugcucacc auuucgacga uuuuucguc ccuuucgggu cuucuuguaa    60
aguuuuuggc uauucuuuuu cuucgcuuuc uccuuccuuu crauacgaua aauguaaaua   120
uuucaugagu uuguucacgu aggacuaugg ccauaaaggu cauuccgaua cucauaguac   180
uugucaaaac auuacuaua aaacuuucu uagcgucgac uucgaagagc aaucgagua    240 auauuauuug caagauguua auguucgucu cuuuaaguuu ggcgucaugc aaauaaugaa   300
ggaccucuua aucgauuugu gcgacaguca cuuccauggu uucgacaaug auuuaugugu   360
ucaagauuc                                                         369
```

```
<210> SEQ ID NO 9
<211> LENGTH: 103
<212> TYPE: PRT
<213> ORGANISM: Diabrotica virgifera

<400> SEQUENCE: 9
```

Met Thr Gly Arg Gly Lys Gly Gly Lys Gly Leu Gly Lys Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

```
<210> SEQ ID NO 10
<211> LENGTH: 122
<212> TYPE: PRT
<213> ORGANISM: Diabrotica virgifera

<400> SEQUENCE: 10
```

Met Pro Pro Lys Thr Ser Gly Lys Ala Ala Lys Lys Ala Gly Lys Ala
1               5                   10                  15

Gln Lys Asn Ile Ser Lys Thr Asp Lys Lys Lys Arg Lys Arg Lys
            20                  25                  30

Glu Tyr Ala Ile Tyr Ile Tyr Lys Val Leu Lys Gln Val His Pro Asp
        35                  40                  45

Thr Gly Ile Ser Ser Lys Ala Met Ser Ile Met Asn Ser Phe Val Asn
    50                  55                  60

Asp Ile Phe Glu Arg Ile Ala Ala Glu Ala Ser Arg Leu Ala His Tyr
65                  70                  75                  80

Asn Lys Arg Ser Thr Ile Thr Ser Arg Glu Ile Gln Thr Ala Val Arg
                85                  90                  95

Leu Leu Leu Pro Gly Glu Leu Ala Lys His Ala Val Ser Glu Gly Thr
            100                 105                 110

Lys Ala Val Thr Lys Tyr Thr Ser Ser Lys
            115                 120

```
<210> SEQ ID NO 11
<211> LENGTH: 19
```

```
<212> TYPE: RNA
<213> ORGANISM: Diabrotica virgifera

<400> SEQUENCE: 11
augacuggac guggaaagg                                              19

<210> SEQ ID NO 12
<211> LENGTH: 19
<212> TYPE: RNA
<213> ORGANISM: Diabrotica virgifera

<400> SEQUENCE: 12
ugacuggacg uggaaaggg                                              19

<210> SEQ ID NO 13
<211> LENGTH: 19
<212> TYPE: RNA
<213> ORGANISM: Diabrotica virgifera

<400> SEQUENCE: 13
gacuggacgu ggaaagggu                                              19

<210> SEQ ID NO 14
<211> LENGTH: 19
<212> TYPE: RNA
<213> ORGANISM: Diabrotica virgifera

<400> SEQUENCE: 14
uuuguacggu uuuggguggu                                             19

<210> SEQ ID NO 15
<211> LENGTH: 19
<212> TYPE: RNA
<213> ORGANISM: Diabrotica virgifera

<400> SEQUENCE: 15
augccuccua agacgagug                                              19

<210> SEQ ID NO 16
<211> LENGTH: 19
<212> TYPE: RNA
<213> ORGANISM: Diabrotica virgifera

<400> SEQUENCE: 16
ugccuccuaa gacgagugg                                              19

<210> SEQ ID NO 17
<211> LENGTH: 19
<212> TYPE: RNA
<213> ORGANISM: Diabrotica virgifera

<400> SEQUENCE: 17
gccuccuaag acgaguggu                                              19

<210> SEQ ID NO 18
<211> LENGTH: 19
<212> TYPE: RNA
<213> ORGANISM: Diabrotica virgifera

<400> SEQUENCE: 18
uaaauacaca aguucuaag                                              19

<210> SEQ ID NO 19
```

```
<211> LENGTH: 19
<212> TYPE: RNA
<213> ORGANISM: Artificial Sequence
<220> FEATURE:
<223> OTHER INFORMATION: DvH4*-1-19mer

<400> SEQUENCE: 19
uacugaccug caccuuucc                                                    19

<210> SEQ ID NO 20
<211> LENGTH: 19
<212> TYPE: RNA
<213> ORGANISM: Artificial Sequence
<220> FEATURE:
<223> OTHER INFORMATION: DvH4*-2-19mer siRNA

<400> SEQUENCE: 20
acugaccugc accuuuccc                                                    19

<210> SEQ ID NO 21
<211> LENGTH: 19
<212> TYPE: RNA
<213> ORGANISM: Artificial Sequence
<220> FEATURE:
<223> OTHER INFORMATION: DvH4*-3-19mer siRNA

<400> SEQUENCE: 21
cugaccugca ccuuccca                                                     19

<210> SEQ ID NO 22
<211> LENGTH: 19
<212> TYPE: RNA
<213> ORGANISM: Artificial Sequence
<220> FEATURE:
<223> OTHER INFORMATION: DvH4*-291-19mer siRNA

<400> SEQUENCE: 22
aaacaugcca aaaccacca                                                    19

<210> SEQ ID NO 23
<211> LENGTH: 19
<212> TYPE: RNA
<213> ORGANISM: Artificial Sequence
<220> FEATURE:
<223> OTHER INFORMATION: DvH2B8-1-19mer siRNA

<400> SEQUENCE: 23
uacggaggau ucugcucac                                                    19

<210> SEQ ID NO 24
<211> LENGTH: 19
<212> TYPE: RNA
<213> ORGANISM: Artificial Sequence
<220> FEATURE:
<223> OTHER INFORMATION: DvH2B*-2-19mer siRNA

<400> SEQUENCE: 24
acggaggauu cugcucacc                                                    19

<210> SEQ ID NO 25
<211> LENGTH: 19
<212> TYPE: RNA
<213> ORGANISM: Artificial Sequence
<220> FEATURE:
<223> OTHER INFORMATION: DvH2B*-3-19mer siRNA

<400> SEQUENCE: 25
```

```
cggaggauuc ugcucacca                                                19
```

```
<210> SEQ ID NO 26
<211> LENGTH: 19
<212> TYPE: RNA
<213> ORGANISM: Artificial Sequence
<220> FEATURE:
<223> OTHER INFORMATION: DvH2B*-351-19mer siRNA

<400> SEQUENCE: 26
auuuaugugu ucaagauuc                                                19
```

```
<210> SEQ ID NO 27
<211> LENGTH: 363
<212> TYPE: DNA
<213> ORGANISM: Diabrotica undecimpunctata

<400> SEQUENCE: 27
cgaaactaat tttaccctaa aaatgactgg acgtggaaaa ggtggtaaag gtttgggaaa      60
aggtggcgct aaacgtcatc gtaaagtatt acgtgataac atccaaggta ttaccaagcc     120
tgctatcaga agactagctc gtcgcggagg agtaaaacgt atttctggtt taatctatga     180
ggaaacgaga ggtgtattga agtattttt ggagaacgtc attagagatg cagttaccta     240
tactgagcac gccaaaagga aaacagtaac tgctatggat gttgtatatg cacttaaacg     300
gcaaggtcgt acgttatatg gttttggtgg ttaattgcta tgaatatgat tcttaaaaca     360
acg                                                                 363
```

```
<210> SEQ ID NO 28
<211> LENGTH: 309
<212> TYPE: DNA
<213> ORGANISM: Diabrotica undecimpunctata

<400> SEQUENCE: 28
atgactggac gtggaaaagg tggtaaaggt ttgggaaaag gtggcgctaa acgtcatcgt      60
aaagtattac gtgataacat ccaaggtatt accaagcctg ctatcagaag actagctcgt     120
cgcggaggag taaaacgtat ttctggttta atctatgagg aaacgagagg tgtattgaaa     180
gtatttttgg agaacgtcat tagagatgca gttacctata ctgagcacgc caaaaggaaa     240
acagtaactg ctatggatgt tgtatatgca cttaaacggc aaggtcgtac gttatatggt     300
tttggtggt                                                           309
```

```
<210> SEQ ID NO 29
<211> LENGTH: 309
<212> TYPE: RNA
<213> ORGANISM: Diabrotica undecimpunctata

<400> SEQUENCE: 29
augacuggac guggaaaagg ugguaaaggu uugggaaaag guggcgcuaa acgucaucgu      60
aaaguauuac gugauaacau ccaagguauu accaagccug cuaucagaag acuagcucgu     120
cgcggaggag uaaaacguau uucugguuua aucuaugagg aaacgagagg uguauugaaa     180
guauuuuugg agaacgucau uagagaugca guuaccuaua cugagcacgc caaaaggaaa     240
acaguaacug cuauggaugu uguauaugca cuuaaacggc aaggucguac guuauaugguu    300 uuuggugguu                                                          309
```

```
<210> SEQ ID NO 30
```

<211> LENGTH: 309
<212> TYPE: RNA
<213> ORGANISM: Artificial Sequence
<220> FEATURE:
<223> OTHER INFORMATION: Antisense strand of DuH4 variant 1 mRNA

<400> SEQUENCE: 30

| uacugaccug caccuuuucc accauuucca aacccuuuuc caccgcgauu ugcaguagca | 60 |
| uuucauaaug cacuauugua gguuccauaa ugguucggac gauagucuuc ugaucgagca | 120 |
| gcgccuccuc auuuugcaua aagaccaaau uagauacucc uuugcucucc acauaacuuu | 180 |
| cauaaaaacc ucuugcagua aucucuacgu caauggauau gacucgugcg guuuuccuuu | 240 |
| ugucauugac gauaccuaca acauauacgu gaauugccg uuccagcaug caauauacca | 300 |
| aaaccacca | 309 |

<210> SEQ ID NO 31
<211> LENGTH: 420
<212> TYPE: DNA
<213> ORGANISM: Diabrotica undecimpunctata

<400> SEQUENCE: 31

| caagtacgtc gacacttatt ttaccgtaaa aatgactgga cgtggaaaag gtggtaaagg | 60 |
| tttgggaaaa ggtggcgcta aacgtcatcg taaagttttg cgtgataaca tccaaggtat | 120 |
| taccaagcct gctatcagaa gattggctcg tcgaggagga gtaaaacgta tttctggctt | 180 |
| aatctatgag gaaacgagag gtgtattgaa agtattttg gaaaacgtta ttagagatgc | 240 |
| tgttacctat actgaacacg ccaagaggaa aacagtaact gctatggatg ttgtgtatgc | 300 |
| acttaaacgc caaggtcgta cttttgtacgg ttttggtggt taatttataa taacaccatc | 360 |
| aacttattta aacaaacggt tcttttcaga gccacaatta attgcttatg tatagaattc | 420 |

<210> SEQ ID NO 32
<211> LENGTH: 309
<212> TYPE: DNA
<213> ORGANISM: Diabrotica undecimpunctata

<400> SEQUENCE: 32

| atgactggac gtggaaaagg tggtaaaggt ttgggaaaag gtggcgctaa acgtcatcgt | 60 |
| aaagttttgc gtgataacat ccaaggtatt accaagcctg ctatcagaag attggctcgt | 120 |
| cgaggaggag taaaacgtat ttctggctta atctatgagg aaacgagagg tgtattgaaa | 180 |
| gtattttgg aaaacgttat tagagatgct gttacctata ctgaacacgc caagaggaaa | 240 |
| acagtaactg ctatggatgt tgtgtatgca cttaaacgcc aaggtcgtac ttttgtacggt | 300 |
| tttggtggt | 309 |

<210> SEQ ID NO 33
<211> LENGTH: 309
<212> TYPE: RNA
<213> ORGANISM: Diabrotica undecimpunctata

<400> SEQUENCE: 33

| augacuggac guggaaaagg ugguaaaggu uugggaaaag guggcgcuaa acgucaucgu | 60 |
| aaaguuuugc gugauaacau ccaagguauu accaagccug cuaucagaag auuggcucgu | 120 |
| cgaggaggag uaaaacguau uucuggcuua aucuaugagg aaacgagagg uguauugaaa | 180 |
| guauuuuugg aaaacguuau uagagaugcu guuaccuaua cugaacacgc caagaggaaa | 240 |
| acaguaacug cuauggaugu uguguaugca cuuaaacgcc aaggucguac uuuguacggu | 300 |

```
uuugguggu                                                            309

<210> SEQ ID NO 34
<211> LENGTH: 309
<212> TYPE: RNA
<213> ORGANISM: Artificial Sequence
<220> FEATURE:
<223> OTHER INFORMATION: Antisense strand of DuH4 variant 2 mRNA

<400> SEQUENCE: 34
uacugaccug caccuuuucc accauuucca aacccuuuuc caccgcgauu ugcaguagca     60
uuucaaaacg cacauugua gguuccauaa ugguucggac gauagucuuc uaaccgagca    120
gcuccuccuc auuuugcaua aagaccgaau uagauacucc uuugcucucc acauaacuuu    180
cauaaaaacc uuuugcaaua aucucuacga caauggauau gacuugugcg guucuccuuu    240 ugcauugac gauaccuaca acacauacgu gaauuugcgg uuccagcaug aaacaugcca    300
aaaccacca                                                           309

<210> SEQ ID NO 35
<211> LENGTH: 103
<212> TYPE: PRT
<213> ORGANISM: Diabrotica undecimpunctata

<400> SEQUENCE: 35

Met Thr Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 36
<211> LENGTH: 690
<212> TYPE: DNA
<213> ORGANISM: Diabrotica undecimpunctata
<220> FEATURE:
<221> NAME/KEY: misc_feature
<222> LOCATION: (504)..(504)
<223> OTHER INFORMATION: n is a, c, g, or t

<400> SEQUENCE: 36
ggggcttacg ccgtattact cattttatta taaaaaaaaa ctgaaagtcg cggaagctag     60
ttttcgtccg actttcaaag agtaaacgtc aatttattcg caatgcctcc taagactagt    120
ggtaaagctg ctaaaaaagc aggaaaagct cagaagaata tttccaagac cgataagaaa    180
aagaagcgta agaggaagga aagttatgcc atttacatct ataaagtatt gaacaagtg     240 catcctgata ctggtatttc cagtaaggct atgagtatca tgaacagttt tgtaaatgat    300 attttgaaa gaattgctgc tgaagcttct cgtttagctc attacaataa acggtcaaca    360
attacaagca gagaaattca aaccgccgta cgtttattac ttcctggaga gttagctaaa    420
```

```
cacgccgtta gtgaaggtac caaagctgtt actaaatata caagttctaa gtaattataa    480
tatttccttt tataaatata acangaagct tctcgtttag ctcattacaa taaacggtca    540
acaattacaa gcagagaaat tcaaaccgcc gtacgtctat tacttcctgg agagttagct    600
aaacacgccg tcagtgaagg taccaaagct gttactaaat atacaagttc taagtaatcc    660
cactacttca tcttacaaat ataaaaaacg                                      690

<210> SEQ ID NO 37
<211> LENGTH: 369
<212> TYPE: DNA
<213> ORGANISM: Diabrotica undecimpunctata

<400> SEQUENCE: 37
atgcctccta agactagtgg taaagctgct aaaaaagcag gaaaagctca gaagaatatt     60
tccaagaccg ataagaaaaa gaagcgtaag aggaaggaaa gttatgccat ttacatctat    120
aaagtattga acaagtgca tcctgatact ggtatttcca gtaaggctat gagtatcatg     180
aacagttttg taaatgatat ttttgaaaga attgctgctg aagcttctcg tttagctcat    240
tacaataaac ggtcaacaat tacaagcaga gaaattcaaa ccgccgtacg tttattactt    300
cctggagagt tagctaaaca cgccgttagt gaaggtacca agctgttac taaatataca     360 agttctaag                                                             369

<210> SEQ ID NO 38
<211> LENGTH: 369
<212> TYPE: RNA
<213> ORGANISM: Diabrotica undecimpunctata

<400> SEQUENCE: 38
augccuccua agacuagugg uaaagcugcu aaaaaagcag gaaaagcuca gaagaauauu     60
uccaagaccg auaagaaaaa gaagcguaag aggaaggaaa guuaugccau uuacaucuau    120
aaaguauuga acaagugca uccugauacu gguauuucca guaaggcuau gaguaucaug    180
aacaguuuug uaaaugauau uuuugaaaga auugcugcug aagcuucucg uuuagcucau    240
uacaauaaac ggucaacaau uacaagcaga gaaauucaaa ccgccguacg uuuauuacuu    300
ccuggagagu uagcuaaaca cgccguuagu gaagguacca agcuguuac uaaauauaca     360 aguucuaag                                                             369

<210> SEQ ID NO 39
<211> LENGTH: 369
<212> TYPE: RNA
<213> ORGANISM: Artificial Sequence
<220> FEATURE:
<223> OTHER INFORMATION: Antisense strand of DuH2B mRNA

<400> SEQUENCE: 39
uacggaggau ucugaucacc auuucgacga uuuuuucguc cuuuucgagu cuucuuauaa     60
agguucuggc uauucuuuuu cuucgcauuc uccuuccuuu caauacggua aauguagaua    120
uuucauaacu uuguucacgu aggacuauga ccauaaaggu cauuccgaua cucauaguac    180
uugucaaaac auuacuaua aaaacuuucu uaacgacgac uucgaagagc aaaucgagua    240
auguuauuug ccaguuguua auguucgucu cuuuaaguuu ggcggcaugc aaauaaugaa    300 ggacccucuca aucgauuugu gcggcaauca cuuccauggu uucgacaaug auuuauaugu    360
ucaagauuc                                                             369
```

<210> SEQ ID NO 40
<211> LENGTH: 123
<212> TYPE: PRT
<213> ORGANISM: Diabrotica undecimpunctata

<400> SEQUENCE: 40

```
Met Pro Pro Lys Thr Ser Gly Lys Ala Ala Lys Ala Gly Lys Ala
1               5                   10                  15

Gln Lys Asn Ile Ser Lys Thr Asp Lys Lys Lys Arg Lys Arg Lys
            20                  25                  30

Glu Ser Tyr Ala Ile Tyr Ile Tyr Lys Val Leu Lys Gln Val His Pro
        35                  40                  45

Asp Thr Gly Ile Ser Ser Lys Ala Met Ser Ile Met Asn Ser Phe Val
    50                  55                  60

Asn Asp Ile Phe Glu Arg Ile Ala Ala Glu Ala Ser Arg Leu Ala His
65                  70                  75                  80

Tyr Asn Lys Arg Ser Thr Ile Thr Ser Arg Glu Ile Gln Thr Ala Val
                85                  90                  95

Arg Leu Leu Leu Pro Gly Glu Leu Ala Lys His Ala Val Ser Glu Gly
            100                 105                 110

Thr Lys Ala Val Thr Lys Tyr Thr Ser Ser Lys
            115                 120
```

<210> SEQ ID NO 41
<211> LENGTH: 495
<212> TYPE: DNA
<213> ORGANISM: Diabrotica barberi

<400> SEQUENCE: 41

```
ggggtacatc ttaatttgga ttggtcgttt ttcgatttgg aggtgtgtca ataattttaa      60
agtacggata tttaaaggtc gaaagacgaa tgcaattcag taattccagg acaactgaac     120
tgattgtatc atgactggac gtggaaaggg tggtaaaggt ttgggaaaag gtggcgctaa     180
acgtcaccgt aaagtgttac gtgacaacat ccaaggtatt accaagcctg ctataagaag     240
attagctcgt cgcggaggtg taaaacgtat ctctggttta atctatgagg aaacgcgagg     300
tgtattgaaa gtattttttgg aaaacgttat tagagatgcc gttacctata ctgagcacgc     360
caaaaggaaa acagtaactg ctatggatgt tgtatatgca cttaaacgac aaggtcgtac     420
tttgtacggt tttggaggtt aattgctatt aatttccatc cttaaaaaaa cggttctttt     480
cagaaccaca aaaaa                                                      495
```

<210> SEQ ID NO 42
<211> LENGTH: 309
<212> TYPE: DNA
<213> ORGANISM: Diabrotica barberi

<400> SEQUENCE: 42

```
atgactggac gtggaaaggg tggtaaaggt ttgggaaaag gtggcgctaa acgtcaccgt      60
aaagtgttac gtgacaacat ccaaggtatt accaagcctg ctataagaag attagctcgt     120
cgcggaggtg taaaacgtat ctctggttta atctatgagg aaacgcgagg tgtattgaaa     180
gtattttttgg aaaacgttat tagagatgcc gttacctata ctgagcacgc caaaaggaaa     240
acagtaactg ctatggatgt tgtatatgca cttaaacgac aaggtcgtac tttgtacggt     300
tttggaggt                                                             309
```

<210> SEQ ID NO 43
<211> LENGTH: 309
<212> TYPE: RNA
<213> ORGANISM: Diabrotica barberi

<400> SEQUENCE: 43

```
augacuggac guggaaaggg ugguaaaggu uugggaaaag guggcgcuaa acgucaccgu    60
aaaguguuac gugacaacau ccaagguauu accaagccug cuauaagaag auuagcucgu   120
cgcggaggug uaaaacguau cucgguuuua aucuaugagg aaacgcgagg uguauugaaa   180
guauuuuugg aaaacguuau uagagaugcc guuaccuaua cugagcacgc caaaggaaaa   240
acaguaacug cuauggaugu uguauaugca cuuaaacgac aaggucguac uuuguacggu   300
uuuggaggu                                                          309
```

<210> SEQ ID NO 44
<211> LENGTH: 309
<212> TYPE: RNA
<213> ORGANISM: Artificial Sequence
<220> FEATURE:
<223> OTHER INFORMATION: Antisense strand of DbH4 mRNA

<400> SEQUENCE: 44

```
uacugaccug caccuuuccc accauuucca aacccuuuuc caccgcgauu ugcaguggca    60
uuucacaaug cacuguugua gguuccauaa ugguucggac gauauucuuc uaaucgagca   120
gcgccuccac auuuugcaua gagaccaaau uagauacucc uuugcgcucc acauaacuuu   180
cauaaaaacc uuuugcaaua aucucuacgg caauggauau gacucgugcg guuuuccuuu   240
ugucauugac gauaccuaca acauauacgu gaauuugcug uuccagcaug aaacaugcca   300
aaaccucca                                                          309
```

<210> SEQ ID NO 45
<211> LENGTH: 103
<212> TYPE: PRT
<213> ORGANISM: Diabrotica barberi

<400> SEQUENCE: 45

```
Met Thr Gly Arg Gly Lys Gly Gly Lys Gly Leu Gly Lys Gly Ala
1               5                   10                  15
Lys Arg His Arg Lys Val Leu Arg Asp Asn Ile Gln Gly Ile Thr Lys
            20                  25                  30
Pro Ala Ile Arg Arg Leu Ala Arg Arg Gly Gly Val Lys Arg Ile Ser
        35                  40                  45
Gly Leu Ile Tyr Glu Glu Thr Arg Gly Val Leu Lys Val Phe Leu Glu
    50                  55                  60
Asn Val Ile Arg Asp Ala Val Thr Tyr Thr Glu His Ala Lys Arg Lys
65                  70                  75                  80
Thr Val Thr Ala Met Asp Val Val Tyr Ala Leu Lys Arg Gln Gly Arg
                85                  90                  95
Thr Leu Tyr Gly Phe Gly Gly
            100
```

<210> SEQ ID NO 46
<211> LENGTH: 448
<212> TYPE: DNA
<213> ORGANISM: Diabrotica barberi

<400> SEQUENCE: 46

```
cgtcagtttg ttttgcgat gcctcctaag acgagtggta aagctgctaa aaaggcagga    60
```

| | |
|---|---|
| aaagcccaga agaacatttc aaaaaccgat aagaaaaaga agcgaaagag gaaggaaagc | 120 |
| tatgctattt acatttataa agtactcaaa caagtgcatc ctgataccgg tatttccagt | 180 |
| aaggctatga gtatcatgaa cagtttgta aatgatattt ttgaaagaat cgctgccgaa | 240 |
| gcttcccgtt tagctcatta taataaacgt tctacaatta caagcagaga aattcaaacg | 300 |
| gccgtacgtt tattacttcc tggagaatta gctaaacacg ctgtcagtga aggcaccaaa | 360 |
| gctgttacta atacacaag ttctaagtaa tcagaacgct tcatctatta attataacaa | 420 |
| acggttcttt tcagaaccac aaaaaaaa | 448 |

<210> SEQ ID NO 47
<211> LENGTH: 369
<212> TYPE: DNA
<213> ORGANISM: Diabrotica barberi

<400> SEQUENCE: 47

| | |
|---|---|
| atgcctccta agacgagtgg taaagctgct aaaaaggcag gaaaagccca gaagaacatt | 60 |
| tcaaaaaccg ataagaaaaa gaagcgaaag aggaaggaaa gctatgctat ttacatttat | 120 |
| aaagtactca acaagtgca tcctgatacc ggtatttcca gtaaggctat gagtatcatg | 180 |
| aacagttttg taatgatat ttttgaaaga atcgctgccg aagcttcccg tttagctcat | 240 |
| tataataaac gttctacaat tacaagcaga gaaattcaaa cggccgtacg tttattactt | 300 |
| cctggagaat tagctaaaca cgctgtcagt gaaggcacca aagctgttac taaatacaca | 360 |
| agttctaag | 369 |

<210> SEQ ID NO 48
<211> LENGTH: 369
<212> TYPE: RNA
<213> ORGANISM: Diabrotica barberi

<400> SEQUENCE: 48

| | |
|---|---|
| augccuccua agacgagugg uaaagcugcu aaaaaggcag gaaaagccca gaagaacauu | 60 |
| ucaaaaaccg auaagaaaaa gaagcgaaag aggaaggaaa gcuaugcuau uuacauuuau | 120 |
| aaaguacuca acaagugca uccugauacc gguauuucca guaaggcuau gaguaucaug | 180 |
| aacaguuuug uaaugauau uuuugaaaga aucgcugccg aagcuucccg uuuagcucau | 240 |
| uauaauaaac guucuacaau uacaagcaga gaaauucaaa cggccguacg uuuauuacuu | 300 |
| ccuggagaau uagcuaaaca cgcugucagu gaaggcacca aagcuguuac uaaauacaca | 360 |
| aguucuaag | 369 |

<210> SEQ ID NO 49
<211> LENGTH: 369
<212> TYPE: RNA
<213> ORGANISM: Artificial Sequence
<220> FEATURE:
<223> OTHER INFORMATION: Antisense strand of DbH2B mRNA

<400> SEQUENCE: 49

| | |
|---|---|
| uacggaggau ucugcucacc auuucgacga uuuuuccguc cuuuucgggu cuucuuguaa | 60 |
| aguuuuggc uauucuuuuu cuucgcuuuc uccuuccuuu cgauacgaua aauguaaaua | 120 |
| uuucaugagu uuguucacgu aggacuaugg ccauaaaggu cauuccgaua cucauaguac | 180 |
| uugucaaaac auuacuaua aaaacuuucu uagcgacggc uucgaagggc aaaucgagua | 240 |
| auauuauuug caagauguua auguucgucu cuuuaaguuu gccggcaugc aaauaaugaa | 300 |

```
ggaccucuua aucgauuugu gcgacaguca cuuccguggu uucgacaaug auuuaugugu    360
ucaagauuc                                                             369
```

<210> SEQ ID NO 50
<211> LENGTH: 123
<212> TYPE: PRT
<213> ORGANISM: Diabrotica barberi

<400> SEQUENCE: 50

```
Met Pro Pro Lys Thr Ser Gly Lys Ala Ala Lys Ala Gly Lys Ala
1               5                   10                  15

Gln Lys Asn Ile Ser Lys Thr Asp Lys Lys Lys Arg Lys Arg Lys
                20                  25                  30

Glu Ser Tyr Ala Ile Tyr Ile Tyr Lys Val Leu Lys Gln Val His Pro
        35                  40                  45

Asp Thr Gly Ile Ser Ser Lys Ala Met Ser Ile Met Asn Ser Phe Val
        50                  55                  60

Asn Asp Ile Phe Glu Arg Ile Ala Ala Glu Ala Ser Arg Leu Ala His
65                  70                  75                  80

Tyr Asn Lys Arg Ser Thr Ile Thr Ser Arg Glu Ile Gln Thr Ala Val
                85                  90                  95

Arg Leu Leu Leu Pro Gly Glu Leu Ala Lys His Ala Val Ser Glu Gly
            100                 105                 110

Thr Lys Ala Val Thr Lys Tyr Thr Ser Ser Lys
            115                 120
```

<210> SEQ ID NO 51
<211> LENGTH: 20
<212> TYPE: DNA
<213> ORGANISM: Diabrotica virgifera

<400> SEQUENCE: 51

```
atgcctccta agacgagtgg                                                 20
```

<210> SEQ ID NO 52
<211> LENGTH: 20
<212> TYPE: DNA
<213> ORGANISM: Diabrotica virgifera

<400> SEQUENCE: 52

```
cttagaactt gtgtatttag                                                 20
```

<210> SEQ ID NO 53
<211> LENGTH: 20
<212> TYPE: DNA
<213> ORGANISM: Diabrotica virgifera

<400> SEQUENCE: 53

```
atgactggac gtggaaaggg                                                 20
```

<210> SEQ ID NO 54
<211> LENGTH: 20
<212> TYPE: DNA
<213> ORGANISM: Diabrotica virgifera

<400> SEQUENCE: 54

```
accaccaaaa ccgtacaaag                                                 20
```

<210> SEQ ID NO 55
<211> LENGTH: 40

<212> TYPE: DNA
<213> ORGANISM: Diabrotica virgifera

<400> SEQUENCE: 55
taatacgact cactataggg atgcctccta agacgagtgg                          40

<210> SEQ ID NO 56
<211> LENGTH: 40
<212> TYPE: DNA
<213> ORGANISM: Diabrotica virgifera

<400> SEQUENCE: 56
taatacgact cactataggg cttagaactt gtgtatttag                          40

<210> SEQ ID NO 57
<211> LENGTH: 40
<212> TYPE: DNA
<213> ORGANISM: Diabrotica virgifera

<400> SEQUENCE: 57
taatacgact cactataggg atgactggac gtggaaaggg                          40

<210> SEQ ID NO 58
<211> LENGTH: 40
<212> TYPE: DNA
<213> ORGANISM: Diabrotica virgifera

<400> SEQUENCE: 58
taatacgact cactataggg accaccaaaa ccgtacaaag                          40

<210> SEQ ID NO 59
<211> LENGTH: 4163
<212> TYPE: DNA
<213> ORGANISM: Artificial Sequence
<220> FEATURE:
<223> OTHER INFORMATION: Diabrotica virgifera virgifera, Zea mays,
      Arabidopsis thaliana

<400> SEQUENCE: 59
ctgcagtgca gcgtgacccg gtcgtgcccc tctctagaga taatgagcat tgcatgtcta    60
agttataaaa aattaccaca tatttttttt gtcacacttg tttgaagtgc agtttatcta   120
tctttataca tatatttaaa ctttactcta cgaataatat aatctatagt actacaataa   180
tatcagtgtt ttagagaatc atataaatga acagttagac atggtctaaa ggacaattga   240
gtatttgac aacaggactc tacagtttta tcttttagt gtgcatgtgt tctccttttt     300
ttttgcaaat agcttcacct atataatact tcatccattt tattagtaca tccatttagg   360
gtttagggtt aatggttttt atagactaat ttttttagta catctatttt attctatttt   420
agcctctaaa ttaagaaaac taaaactcta ttttagtttt tttatttaat aatttagata   480
taaaatagaa taaaataaag tgactaaaaa ttaaacaaat acccctttaag aaattaaaaa  540
aactaaggaa acatttttct tgtttcgagt agataatgcc agcctgttaa acgccgccga   600
cgagtctaac ggacaccaac cagcgaacca gcagcgtcgc gtcgggccaa gcgaagcaga   660
cggcacggca tctctgtcgc tgcctctgga cccctctcga gagttccgct ccaccgttgg   720
acttgctccg ctgtcggcat ccagaaattg cgtggcggag cggcagacgt gagccggcac   780
ggcaggcggc ctcctcctcc tctcacggca ccggcagcta cgggggattc ctttcccacc   840
gctccttcgc tttcccttcc tcgcccgccg taataaatag acaccccctc cacaccctct   900
ttccccaacc tcgtgttgtt cggagcgcac acacacacaa ccagatctcc cccaaatcca   960

```
cccgtcggca cctccgcttc aaggtacgcc gctcgtcctc cccccccccc cctctctacc    1020
ttctctagat cggcgttccg gtccatagtt agggcccggt agttctactt ctgttcatgt    1080
ttgtgttaga tccgtgtttg tgttagatcc gtgctgttag cgttcgtaca cggatgcgac    1140
ctgtacgtca gacacgttct gattgctaac ttgccagtgt ttctctttgg ggaatcctgg    1200
gatggctcta gccgttccgc agacgggatc gatttcatga ttttttttgt ttcgttgcat    1260
agggtttggt ttgccctttt cctttatttc aatatatgcc gtgcacttgt ttgtcgggtc    1320
atcttttcat gcttttttt gtcttggttg tgatgatgtg gtctggttgg gcggtcgttc    1380
tagatcggag tagaattctg tttcaaacta cctggtggat ttattaattt tggatctgta    1440
tgtgtgtgcc atacatattc atagttacga attgaagatg atggatggaa atatcgatct    1500
aggataggta tacatgttga tgcgggtttt actgatgcat atacagagat gcttttttgtt   1560 cgcttggttg tgatgatgtg gtgtggttgg gcggtcgttc attcgttcta gatcggagta    1620
gaatactgtt tcaaactacc tggtgtattt attaattttg gaactgtatg tgtgtgtcat    1680
acatcttcat agttacgagt ttaagatgga tggaaatatc gatctaggat aggtatacat    1740
gttgatgtgg gttttactga tgcatataca tgatggcata tgcagcatct attcatatgc    1800
tctaaccttg agtacctatc tattataata aacaagtatg ttttataatt attttgatct    1860
tgatatactt ggatgatggc atatgcagca gctatatgtg gattttttta gccctgcctt    1920
catacgctat ttatttgctt ggtactgttt cttttgtcga tgctcaccct gttgtttggt    1980
gttacttctg cagggatcct gcctcctaag acgagtggta aagctgctaa aaaagcaggg    2040
aaagcccaga gaacatttc aaaaaccgat aagaaaaaga agcgaaagag gaaggaaagc    2100
tatgctattt acatttataa agtactcaaa caagtgcatc ctgataccgg tatttccagt    2160
aaggctatga gtatcatgaa cagttttgta aatgatattt ttgaaagaat cgcagctgaa    2220
gcttctcgtt tagctcatta taataaacgt tctacaatta caagcagaga aattcaaacc    2280
gcagtacgtt tattacttcc tggagaatta gctaaacacg ctgtcagtga agctaccaaa    2340
gctgttacta aatacacaag ttctaagggt accaagctgc gaatcttcgt ttttttaagg    2400
aattctcgat ctttatggtg tataggctct gggttttctg ttttttgtat ctcttaggat    2460
tttgtaaatt ccagatcttt ctatggccac ttagtagtat atttcaaaaa ttctccaatc    2520
gagttcttca ttcgcatttt cagtcatttt ctcttcgacg ttgttttta gcctgggtat    2580 tactcctatt tagttgaact ctgcagcaat cttagaaaat tagggttttg aggtttcgat    2640
ttctctaggt aaccgatcta ttgcattcat ctgaatttct gcatatatgt cttagatttc    2700
tgataagctt acgatacgtt aggtgtaatt gaagtttatt tttcaagagt gttattttt    2760 gtttctgaat ttttcagtca ctccatggct tagaacttgt gtatttagta acagctttgg    2820
tagcttcact gacagcgtgt ttagctaatt ctccaggaag taataaacgt actgcggttt    2880
gaatttctct gcttgtaatt gtagaacgtt tattataatg agctaaacga gaagcttcag    2940
ctgcgattct ttcaaaaata tcatttacaa aactgttcat gatactcata gccttactgg    3000
aaataccggt atcaggatgc acttgtttga gtactttata aatgtaaaata gcatagcttt    3060 ccttcctctt tcgcttcttt ttcttatcgg ttttttgaaat gttcttctgg gctttccctg    3120
cttttttagc agctttacca ctcgtcttag gaggcagagc tcgccatcag tcgttgaagc    3180
tgctgctgta tctgggttat ctagtgtctc tgccattgcc caaggatggt gctgtctttc    3240
aaagtatttg tatggtttgt gtcgtgagtc gtgactgagc tggtttcatg gaccagttgt    3300
```

| | | | | |
|---|---|---|---|---|
| gttctcgtta | cccaaaacta | tcgtgcgacc | gcatatggct | taatcatgaa | taaatgttgt | 3360 |
| ttgaatttaa | actattcgct | gaatattgtt | gttttttgtc | atgtcagtta | atgttactaa | 3420 |
| attggttgcc | ttctaatttt | tgtttactgg | tgtttgtcgc | accttatctt | tttactgtat | 3480 |
| gtttacttca | ggttctggca | gtctcatttt | tgtgactag | ttaaaactta | cagctaaaaa | 3540 |
| aatgcagttt | ttcattttca | tttgaagttt | gattagagct | attgataccc | ggaccatcag | 3600 |
| gttaggttag | ttgtgcatag | aatcataaat | attaatcatg | ttttctatga | attaagtcaa | 3660 |
| acttgaaagt | ctggctgaat | atagtttcta | tgaatcatat | tgatatacat | gtttgattat | 3720 |
| ttgttttgct | attagctatt | tactttggtg | aatctatata | ggcttatgca | gaaccttttt | 3780 |
| ttttgttcta | tatatccata | tcctagtact | cagtagctct | atgttttctg | gagactagtg | 3840 |
| gcttgctttt | tcgtatgtct | aattttttgc | ttgaccattg | caaaacaaaa | attacctagt | 3900 |
| gtaatctctt | tttataataa | tcttgtaatg | cgtctaccta | taggtcaaag | taggttttgt | 3960 |
| ttggaaccct | tagagctaac | tgttagctag | ttgataaatt | attagctgag | ttaagctagc | 4020 |
| taatgaacta | gttttgatat | tagctgagga | tgtttgaaac | ctaataatta | ttttttatta | 4080 |
| gctaactata | ctaaattta | gtagagagat | tccaaacagg | agttaacatg | ggatcagatt | 4140 |
| ggctatgcgt | ttgcaatccc | ata | | | | 4163 |

<210> SEQ ID NO 60
<211> LENGTH: 4043
<212> TYPE: DNA
<213> ORGANISM: Artificial Sequence
<220> FEATURE:
<223> OTHER INFORMATION: Diabrotica virgifera virgifera, Zea mays,
    Arabidopsis thaliana

<400> SEQUENCE: 60

| | | | | | | |
|---|---|---|---|---|---|---|
| ctgcagtgca | gcgtgacccg | gtcgtgcccc | tctctagaga | taatgagcat | tgcatgtcta | 60 |
| agttataaaa | aattaccaca | tatttttttt | gtcacacttg | tttgaagtgc | agtttatcta | 120 |
| tctttataca | tatatttaaa | ctttactcta | cgaataatat | aatctatagt | actacaataa | 180 |
| tatcagtgtt | ttagagaatc | atataaatga | acagttagac | atggtctaaa | ggacaattga | 240 |
| gtattttgac | aacaggactc | tacagtttta | tcttttagt | gtgcatgtgt | tctccttttt | 300 |
| ttttgcaaat | agcttcacct | atataatact | tcatccattt | tattagtaca | tccatttagg | 360 |
| gtttagggtt | aatggttttt | atagactaat | ttttttagta | catctatttt | attctatttt | 420 |
| agcctctaaa | ttaagaaaac | taaaactcta | ttttagtttt | tttatttaat | aatttagata | 480 |
| taaaatagaa | taaaataaag | tgactaaaaa | ttaaacaaat | acccttttaag | aaattaaaaa | 540 |
| aactaaggaa | acattttttct | tgtttcgagt | agataatgcc | agcctgttaa | acgccgccga | 600 |
| cgagtctaac | ggacaccaac | cagcgaacca | gcagcgtcgc | gtcgggccaa | gcgaagcaga | 660 |
| cggcacggca | tctctgtcgc | tgcctctgga | cccctctcga | gagttccgct | ccaccgttgg | 720 |
| acttgctccg | ctgtcggcat | ccagaaattg | cgtggcggag | cggcagacgt | gagccggcac | 780 |
| ggcaggcggc | ctcctcctcc | tctcacggca | ccggcagcta | cgggggattc | ctttcccacc | 840 |
| gctccttcgc | tttcccttcc | tcgcccgccg | taataaatag | acaccccctc | cacaccctct | 900 |
| ttccccaacc | tcgtgttgtt | cggagcgcac | acacacacaa | ccagatctcc | cccaaatcca | 960 |
| ccgtcggca | cctccgcttc | aaggtacgcc | gctcgtcctc | ccccccccc | cctctctacc | 1020 |
| ttctctagat | cggcgttccg | gtccatagtt | agggcccggt | agttctactt | ctgttcatgt | 1080 |
| ttgtgttaga | tccgtgtttg | tgttagatcc | gtgctgttag | cgttcgtaca | cggatgcgac | 1140 |

```
ctgtacgtca gacacgttct gattgctaac ttgccagtgt ttctctttgg ggaatcctgg     1200
gatggctcta gccgttccgc agacgggatc gatttcatga ttttttttgt ttcgttgcat     1260
agggtttggt ttgcccttt cctttatttc aatatatgcc gtgcacttgt ttgtcgggtc     1320
atcttttcat gcttttttt gtcttggttg tgatgatgtg gtctggttgg gcggtcgttc     1380
tagatcggag tagaattctg tttcaaacta cctggtggat ttattaattt tggatctgta     1440
tgtgtgtgcc atacatattc atagttacga attgaagatg atggatggaa atatcgatct     1500
aggataggta tacatgttga tgcgggtttt actgatgcat atacagagat gcttttgtt      1560 cgcttggttg tgatgatgtg gtgtggttgg gcggtcgttc attcgttcta gatcggagta     1620
gaatactgtt tcaaactacc tggtgtattt attaattttg gaactgtatg tgtgtgtcat     1680
acatcttcat agttacgagt ttaagatgga tggaaatatc gatctaggat aggtatacat     1740
gttgatgtgg gttttactga tgcatataca tgatggcata tgcagcatct attcatatgc     1800
tctaaccttg agtacctatc tattataata aacaagtatg ttttataatt attttgatct     1860
tgatatactt ggatgatggc atatgcagca gctatatgtg gatttttta gccctgcctt      1920 catacgctat ttatttgctt ggtactgttt cttttgtcga tgctcaccct gttgtttggt     1980
gttacttctg cagggatcct gactggacgt ggaaagggtg gtaaaggttt gggcaaaggt     2040
ggcgctaaac gtcaccgtaa agtattacgt gacaacatcc aaggtattac caagcctgct     2100
ataagaagat tagctcgtcg cggaggtgta aaacgtatct ctggtttaat ctatgaggaa     2160
acgcgaggtg tattgaaagt atttttggaa aacgttatta gagatgccgt tacctatact     2220
gagcacgcca aaaggaaaac agtaactgct atggatgttg tatatgcact taaacgacaa     2280
ggtcgtactt tgtacggttt tggtggtggt accaagctgc gaatcttcgt ttttttaagg     2340
aattctcgat ctttatggtg tataggctct gggttttctg tttttgtat ctcttaggat      2400 tttgtaaatt ccagatcttt ctatggccac ttagtagtat atttcaaaaa ttctccaatc     2460
gagttcttca ttcgcatttt cagtcatttt ctcttcgacg ttgttttta gcctgggtat      2520 tactcctatt tagttgaact ctgcagcaat cttagaaaat tagggttttg aggtttcgat     2580
ttctctaggt aaccgatcta ttgcattcat ctgaatttct gcatatatgt cttagatttc     2640
tgataagctt acgatacgtt aggtgtaatt gaagtttatt tttcaagagt gttattttt      2700 gtttctgaat ttttcagtca ctccatggac caccaaaacc gtacaaagta cgaccttgtc     2760
gtttaagtgc atatacaaca tccatagcag ttactgtttt ccttttggcg tgctcagtat     2820
aggtaacggc atctctaata acgttttcca aaaatacttt caatacacct cgcgtttcct     2880
catagattaa accagagata cgttttacac ctccgcgacg agctaatctt cttatagcag     2940
gcttggtaat accttggatg ttgtcacgta atactttacg gtgacgttta gcgccaccttt    3000 tgcccaaacc tttaccaccc tttccacgtc cagtcagagc tcgccatcag tcgttgaagc     3060
tgctgctgta tctgggttat ctagtgtctc tgccattgcc caaggatggt gctgtctttc     3120
aaagtatttg tatggtttgt gtcgtgagtc gtgactgagc tggtttcatg gaccagttgt     3180
gttctcgtta cccaaaacta tcgtgcgacc gcatatggct taatcatgaa taaatgttgt     3240
ttgaatttaa actattcgct gaatattgtt gtttttgtc atgtcagtta atgttactaa      3300
attggttgcc ttctaatttt tgtttactgg tgtttgtcgc accttatctt tttactgtat     3360
gtttacttca ggttctggca gtctcatttt ttgtgactag ttaaaactta cagctaaaaa     3420
aatgcagttt ttcatttca tttgaagttt gattagagct attgataccc ggaccatcag      3480
gttaggttag ttgtgcatag aatcataaat attaatcatg ttttctatga attaagtcaa     3540
```

```
acttgaaagt ctggctgaat atagtttcta tgaatcatat tgatatacat gtttgattat    3600
ttgttttgct attagctatt tactttggtg aatctatata ggcttatgca gaaccttttt    3660
ttttgttcta tatatccata tcctagtact cagtagctct atgttttctg gagactagtg    3720
gcttgctttt tcgtatgtct aattttttgc ttgaccattg caaaacaaaa attacctagt    3780
gtaatctctt tttataataa tcttgtaatg cgtctaccta taggtcaaag taggttttgt    3840
ttggaaccct tagagctaac tgttagctag ttgataaatt attagctgag ttaagctagc    3900
taatgaacta gttttgatat tagctgagga tgtttgaaac ctaataatta tttttttatta  3960 gctaactata ctaaatttta gtagagagat tccaaacagg agttaacatg ggatcagatt    4020
ggctatgcgt ttgcaatccc ata                                            4043

<210> SEQ ID NO 61
<211> LENGTH: 19
<212> TYPE: RNA
<213> ORGANISM: Artificial Sequence
<220> FEATURE:
<223> OTHER INFORMATION: derived from Diabrotica virgifera

<400> SEQUENCE: 61
acuggucgcg uugcaugcu                                                   19
```